United States Patent [19]
Luo

[11] Patent Number: 5,985,859
[45] Date of Patent: Nov. 16, 1999

[54] METHODS OF INHIBITING BACTERIAL SIALIDASE

[75] Inventor: Ming Luo, Birmingham, Ala.

[73] Assignee: The University of Alabama, Birmingham, Ala.

[21] Appl. No.: 08/485,380

[22] Filed: Jun. 7, 1995

Related U.S. Application Data

[63] Continuation-in-part of application No. 08/227,549, Apr. 14, 1994, Pat. No. 5,453,533.
[51] Int. Cl.$^6$ .......................... A01N 57/14; A01N 37/10; A01N 37/44; A61R 31/66
[52] U.S. Cl. ........................ 514/109; 514/561; 514/888; 514/507; 514/517; 514/518; 514/519; 560/142; 560/145; 560/147; 560/155; 560/156; 560/179; 560/184; 560/205
[58] Field of Search ..................................... 514/109, 561, 514/888, 520, 507, 517, 518, 519; 560/142, 145, 147, 155, 156, 179, 184, 205

[56] References Cited

U.S. PATENT DOCUMENTS

| | | | |
|---|---|---|---|
| 3,691,166 | 9/1972 | Bolhofer et al. | 260/250 R |
| 3,912,723 | 10/1975 | Miller | 260/239 |
| 4,478,823 | 10/1984 | Sanderson | 424/194.1 |
| 4,515,948 | 5/1985 | Kompis et al. | 544/325 |
| 4,537,769 | 8/1985 | Cerini | 424/210.1 |
| 4,659,818 | 4/1987 | Kompis et al. | 544/163 |
| 4,990,537 | 2/1991 | Okuyama et al. | 514/634 |
| 5,108,993 | 4/1992 | De Simone | 514/50 |
| 5,360,817 | 11/1994 | Von Izstein et al. | 514/459 |
| 5,453,533 | 9/1995 | Luo et al. | 560/142 |

FOREIGN PATENT DOCUMENTS

| | | |
|---|---|---|
| 183139 | 5/1980 | Czechoslovakia . |
| 0350840 A2 | 1/1990 | European Pat. Off. . |
| 0 434432 B1 | 6/1991 | European Pat. Off. . |

OTHER PUBLICATIONS

P. Meindl, et al., Inhibition of Neuraminidase Activity by Derivatives of 2–Deoxy–2,3–dehydro–N–acetylneuraminic Acid, Virology, 58, 457–463 (1974).

P. Palese and R.W. Compans, Inhibition of Influenza Virus Replication in Tissue Culture by 2–Deoxy–2,3–dehydro–N–trifluoroacetylneuraminic acid (FANA): Mechanism of Action, J. Gen. Virology, 33, 159–163 (1976).

Crennell, S.J., et al., Crystal structure of a bacterial sialidase (from *Salmonella typhimurium* LT2) shows the same fold as an influenza virus neuraminidase), Proc. Natl. Acad. Sci. USA 90:9852–9856 (1993).

Miller, C.A., et al., Mechanism of Arthrobacter sialophilus Neuraminidase: The Binding of Substrates and Transition–State Analogs, Biochemical and Biophysical Research Communications, 83:1479–1487 (1978).

Flashner, M., et al., The Interaction of Substrate–Related Ketals with Bacterial and Viral Neuraminidases, Archives of Biochemistry and Biophysics 221:188–196 (1983).

G.M. Air and W.G. Laver, "The Neuraminidase of Influenza Virus," *Proteins: Structure, Function, and Genetics*, 6, 341–356 (1989).

P. Bossart–Whitaker, et al., "Three–Dimensional Structure of Influenza A N9 Neuraminidase and its Complex with the Inhibitor 2–Deoxy–2,3–dehydro–N–acetyl Neuraminic Acid," *J. Mol. Biol.*, 232, 1069–1089, (1993).

K. W. Brammer, et al., Antiviral Properties of 1–Phenoxymethyl–3,4–dihydro– and 1,2,3,4–Tetrahydroisoquinolines, *Nature*, 219, 515–517 (1968).

R. Brossmer, et al., "Inhibition Studies on Vibrio cholerae Neuraminidase," *Hoppe–Seyler's Z. Physiol. Chem.*, 358, 391–396 (1977).

G. Bruno and L. Randaccio, "A Refinement of the Benzoic Acid Structure at Room Temperature," *Acta Cryst.*, B36, 1711–1712 (1980).

R.F. Bryan, et al., "3–(p–Bromobenzoyl)–1, 3–thiazolidine–2–thione," *Acta Cryst.*, B36, 1709–1710 (1980).

W.P. Burmeister, et al., "The 2.2 Å Resolution Crystal Structure of Influenza B Neuraminidase and its Complex with Sialic Acid," *EMBO J.*, 11, No. 1, 49–56 (1992).

(List continued on next page.)

*Primary Examiner*—Gary Geist
*Assistant Examiner*—Rosalynd A. Keys
*Attorney, Agent, or Firm*—Needle & Rosenberg, P.C.

[57] ABSTRACT

A method of inhibiting bacterial sialidase comprising administering to a subject an inhibiting effective amount of a compound of formula I:

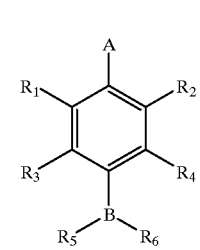

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof. A method of preventing a bacterial or trypanosomal infection using the compounds of formula I. A method of treating a bacterial or trypanosomal infection using the compounds of formula I. A pharmaceutical composition comprising a pharmaceutically acceptable carrier admixed with an inhibiting effective amount of a compound of formula I. A method of making a pharmaceutical composition, comprising admixing a pharmaceutically acceptable carrier with an inhibiting effective amount of a compound of formula I.

11 Claims, 4 Drawing Sheets

OTHER PUBLICATIONS

P.A. Carpy and J.L. Goursolle, "Acide [Dichloro–2, 3(Thenoyl–2)–4 Phenoxy] Acetique (Acide Tienilique)," *Acta Cryst.*, B36, 1706–1708 (1980).

G.P. Ellis and R.T. Jones, "One–Step Synthesis and Spectral Study of Some 1–Methyl–benzimidazoles, Including Use of a Lanthanide Shift Reagent," *J. Chem. Soc. Perk. Trans. I*, 8, 903–909 (1974).

P.H. Gozlan and C. Riche, "Analogues de la Noradrenaline. Structure Cristalline de la (Methylene Dioxy–3',4')–phenyl–2 Hydroxy–2 Acetamideoxime," *Acta Cryst.*, B32, 1662–1665 (1976).

T.H. Haskell, et al., "Neuraminidase Inhibition and Chemotherapy," *J. Med. Chem.*, 13, 697–704 (1970).

M.N. Janakiraman, et al., "Structure Evidence for Hydrolysis Catalyzed by Influenza Virus Neuraminidase Driven by Stabilization of the Oxocarbonium Ion Intermediate," *Biochemistry*, 33, 8172–8179 (1994).

Y. Kageyama, et al., "Structure of the Photostable Form of p–Nitrocinnamic acids," *Acta Cryst.*, C49, 833–834 (1993).

F. Kasuya, et al., "Metabolism of Benoxinate in Humans," *J. Pharm. Sci.*, 76, 303–305 (1987).

T. Kudo, et al., "Syntheses of the Potent Inhibitors of Neuraminidase. N–(1,2–Dihydroxypropyl) Derivatives of Siastatin B and its 4–Deoxy Analogs," *J. Antibiot.*, 46, 300–309 (1993).

V. Kumar, et al., "Methyl 5–Acetamido–2,6–anhydro–3, 5–dideoxy–D–manno–non–2–en–4–ulosonate," *Carbohyd.. Res.*, 103, 281–285 (1982).

R.M. Metzger, et al., "Crystal Structure of DMAP–C–H-MTCAQ, $C_{30}$ $H_{20}N_6O_2N,N$, N–dimethylaminophenylcarbamate–2'–hydroxymethyl–11, 11,12,12–tetracyano–anthraquinodimethan," *J. Cryst, Spect. Research.*, 19(3), 475–482 (1989).

R.M. Metzger, et al., "Structure of MAP:MNA, the 1:1 Adduct Between (R)Methyl12–(2,4–Dinitroanilino)propanoate (MAP) and 2–Methyl–4–nitroaniline (MNA), a New Nonlinear Optical Crystal," *Acta Cryst.*, C49, 738–741 (1993).

T. Nagai, et al., "In Vivo Anti–Influenza Virus Activity of Plant Flavonoids Possessing Inhibitory Activity for Influenza Virus Sialidase," *Antiviral Res.*, 19, 207–217 (1992).

G.O'Neill, "Have Aussies Found a Cure for the Flu?" *J. NIH Res.*, 5, 40–42 (1993).

B.B. Nielsen and I.K. Larsen, "3,4,5–Trihydroxybenzohydroxamic Acid Monohydrate, A Ribonucleotide Reductase Inhibitor," *Acta Cryst.*, C49, 810–813 (1993).

E. Schreiner, et al., "Synthesis of Some 2,3–Didehydro–2–deoxysialic Acids Structurally Varied at C–4 and their Behavior Towards Sialidase from Vibrio cholerae," *Liebigs Ann. Chem.*, 129–134 (1991).

S. Soundarajan, et al., "Structure of 4–Carboxy–2–nitrobenzeneboronic Acid," *Acta Cryst.* C49 690–693 (1993).

N.R. Taylor, et al., "Molecular Modeling Studies on Ligand Binding to Sialiase from Influenza Virus and the Mechanism of Catalysis," *J. Med. Chem.*, 37, 616–624 (1994).

W.R. Tulip, et al., "Refined Atomic Structures of N9 Subtype Influenza Virus Neuraminidase and Escape Mutants," *J. Mol. Biol.*, 221, 487–497 (1991).

W.R. Tulip, et al., "Refined Crystal Structure of the Influenza Virus N9 Neuraminidase–NC41 Fab Complex," *J. Mol. Biol.*, 227, 122–148 (1992).

J.N. Varghese, et al., "The Structure of the Complex Between Influenza Virus Neuraminidase and Sialic Acid, the Viral Receptor," *Proteins: Structure, Function and Genetics*, 14, 327–332 (1992).

A. Vasella and R. Wyler, "Synthesis of a Phosphonic Acid Analogue of N–Acetyl–2,3–didehydro–2–deoxyneuraminic Acid, and Inhibitor of Vibrio cholerae Sialidase," *Helv. Chim. Acta*, 74, 451–463 (1991).

R. Varma and I. Kahn, "Syntheses of Indophenazines and 6–Piperidino/morpholinomethyl–indophenazines As Possible Excystment and Cysticidal Agents," *J. Ind. Chem. Soc.*, 55, 1043–1045 (1978).

L.M. Von Itzstein, et al., "Derivatives and Analogues of 2–Deoxy–2,3–didehydro–N–acetylneuraminic Acid and their Use as Antiviral Agents," *Intern. Patent WO 91/16320* (Oct. 31, 1994).

Crennell, S., et al., "Crystal structure of Vibrio cholerae neuraminidase reveals dual lectin–like domains in addition to the catalytic domain", Structure 2:535–544 (1994).

Drzeniek, R., "Viral Bacterial Neuraminidases", Current Topics in Microbiology & Immunology, 59:35–74 (1972).

Warner, T.G., et al., "Photolabelling of *Salmonella typhimurium* LT2 sialidase,", Biochem. J. 285:957–964 (1992).

Hoyer, L.L., et al., "Purification and Properties of Cloned *Salmonella typhimurium* LT2 Sialidase with Virus–Typical Kinetic Preference for Sialyl $\alpha 2 \to 3$", J. Biochem. 110:462–467 (1991).

Holzer, C.T., et al., "Inhibition of sialidases from viral, bacterial and mammalian sources by analogues of 2–deoxy–2,3–didehydro–N–acetylneuraminic acid modified at the C–4 position", Glycoconjugate Journal 10:40–44 (1993).

Aymard–Henry, M., et al., "Influenzavirus neuraminidase and neuraminidase–inhibition test procedures", Bull. Wld Hlth Org. 45:119–124 (1971).

Pereira, M.E.A., et al., "The Trypanosoma cruzi Neuraminidase Contains Sequences Similar to Bacterial Neuraminidases, YWTD Repeats of the Low Density Lipoprotein Receptor, and Type III Modules of Fibronectin", J. Ex. Med. 174:179–191 (1991).

Gross, G.A.M. & Takle, G.B., "The Surface Trans–Sialidase Family of Trypanosoma Cruzi", Annu. Rev. Microbiol. 47:385–411 (1993).

Schenkman, R.P.F., "Mammalian Cell Sialic Acid Enhances Invasion by Trypanosoma cruzi", Infection and Immunity 61:898–902 (1993), Mar.

Kleineidam, R.G., et al., "4–Methylumbelliferyl–α–Glycosides od Partially Oacetylated N–Acetylneuraminic Acids as Substrates of Bacterial and Viral Sialidases", Biol. Chem. Hoppe–Seyler 371:715–719 (1990).

Scudder, P., et al., "Enzymatic Characterization of β–D–Galactoside α2,3–trans–Sialidse from Trypanosoma cruzi" The Journal of Biological Chemistry 268:9886–9891 (1993).

Vandekerckhove, F., "Substrate specificity of the Trypanosoma cruzi trans–sialidase", Glycobiology 2:541–548 (1992).

Takle, G.B., & Cross, G.A.M., "An 85–kilodalton surface antigen gene family of Trypanosoma cruzi encodes polypeptides homologous to bacterial neuraminidases", Molecular and Biochemical Parasitology 48:185–198 (1991).

Hall, F.B. & Joiner, K.A., "Developmentally–Regulated Virulence Factors of Trypansoma cruzi and Their Relationship to Evasion of Host Defences" J. Euk. Microbiol. 40(2):207–213 (1993).

Childs, W. D. & Gibbons, R. J. (1990). Selective modulation of bacterial attachment to oral epithelial cells by enzyme activities associated with poor oral hygiene. *Journal of Periodontal Research* 25(3), 172–8.

Liljemark, W. F., Bloomquist, C. G., Fenner, L. J., Antonelli, P.J. & Coulter, M.C. (1989). Effect of neuraminidase on the adherence to salivary pellicle of Streptococcus sanguis and Streptococcus mitis. *Caries Research* 23:141–145.

Nakato, H., Shinomiya, K. & Mikawa, H. (1986). Possible role of neuraminidase in the pathogenesis of arteritis and thrombocytopenia induced in rats by Erysipelothrix rhusiopathiae. *Pathology, Research & Practice* 181(3), 311–9.

Cacalano, G., Kays, M., Saiman, L. & Prince, A. (1992). Production of the Pseudomonas aeruginosa neuraminidase is increased under hypersmolar conditions and is regulated by genes involved in alginate expression. *Journal of clinical Investigation* 89(6), 1866–74.

Costello, A. H., Cisar, J.O., Kolenbrander, P.E. & Gabriel, O. (1979). Neuraminidase–dependent hamagglutination of human erythrocytes by human strains of Actinomyces viscosus and Actinomyces naeslundii. *Infection & Immunity* 26(2), 563–72.

Guzman, C. A., Plate, M. & Pruzzo, C. (1990). Role of neuraminidase–dependent adherence in Bacteroides fragilis attachment to human epithelial cells. *FEMS Microbiology Letters* 71, 187–92.

Briselden, A. M., Moncla, B. J., Stevens, C. E. & Hillier, S. L. (1992). Sialidases (neuraminidases) in bacterial vaginosis and bacterial vaginosis–associated microflora. *Journal of Clinical Microbiology* 30(3), 663–6.

LaMarco, K. K., Diven, W. F. & Glew, R. H. (1996). Experimental alteration of chinchilla middle ear mucosae by bacterial neuraminidase. *Annals of Otology, Rhinology & Laryngology* 95(3 Pt 1), 304–8.

Marchand, N.W., Kishore, G.S. & Carubelli, R. (1978). Neuraminidase activity in the blood and liver of arthritic rats. *Experimental & Molecular Pathology* 29(3), 273–80.

Seger, R., Joller, P., Baerlocher, K., Kenny, A., Dulake, C., Leumann, E., Spierig, M. & Hitzig, W. H. (1980). Hemolytic–uremic syndrome associated with neuraminidase–producing microorganisms: treatment by exchange transfusion. *Helvetica Paediatrica Acta* 35(4), 359–67.

Milligan, T. W., Baker, C. J., Straus, D. C. & Mattingly, S. J. (1978). Association of elevated levels of extracellular neuraminidase with clinical isolates of type III group B streptococci. *Infection & Immunity* 21(3), 738–46.

Mosquera, J. & Rodriguez–Iturbe, B. (1984). Extracellular neuraminidase production of streptococci associated with acute nephritis. *Clinical Nephrology* 21(1), 21–8.

Hoffler, U., Gloor, M. & von Nicolai, H. (1981). Neuraminidase production by Propionibacterium acnes–strains isolated from patients with acne vulgaris, seborrheic eczema and healthy subjects. *Zentralblatt Fur Bakteriologie, Mikrobiologie Und Hygiene*—250(1–2), 122–6.

Chemical Abstracts, "Hetaro polyacid salts as antitumor agents," 113:109310D, p. 79, 1990.

Chemical Abstracts, "Preparation of guanidinobenzoic acid amides as antiviral agents," 115:182869P, p. 879, 1991.

Chemical Abstract, vol. 111, No. 9, Aug. 28, 1989, Abstract No. 77591m(p. 713, col. 2) Lee et al., Reactions of amides with potassium permanganate in neutral aqueous solution.

Chemical Abstracts, vol. 93, No. 5, Aug. 4, 1980, Abstract No. 46132t(p. 877, col. 2) Shcherbina et al., Synthesis of p–aminobenzoic acid and its halogen derivatives by the liquid phase catalytic oxidation of N–acylated p–toluidines.

Chemical Abstracts, vol. 68, No. 3, Jan. 15, 1968, Abstract No. 12646g(p. 1197), col. 1) Carter et al., The synthesis of some highly substituted benzene derivatives and several new biphenyls.

Chemical Abstracts, vol. 78, No. 1, Jan. 8, 1973, Abstract No. 228r(p. 20, col. 1) Muldoon et al., Effect of isoprinosine against influenza and some other viruses causing respiratory diseases.

Nielson et al., "Synthesis of Tetranitrotoluenes", *J. Org. Chem.*, 59(7), pp. 1714–1718, 1994.

METHODS OF INHIBITING BACTERIAL SIALIDASE

This application is a continuation-in-part of U.S. Ser. No. 08/227,549, filed Apr. 14, 1994, now U.S. Pat. No. 5,453,533, the contents of which are hereby incorporated fully by this reference.

GOVERNMENT INTEREST

This application has been supported by two grants from the United States National Institutes of Health: R01 AI26718 to Dr. Gillian Air and U01 AI31888 to Dr. Ming Luo and a grant from the National Aeronautics and Space Administration: NAGW-813 to Dr. Larry Delucas.

BACKGROUND

1. Field of the Invention

This invention relates to methods of and pharmaceutical compositions for inhibiting bacterial sialidase and pharmaceutical compositions thereof. In particular, this invention provides novel methods of inhibiting bacterial sialidase, modes of administration of the compounds used in the methods, and pharmaceutical compositions for those methods.

2. Background of the Invention

Sialidases (acylneuraminyl hydrolases, EC 3.2.1.18), also known as neuramninidases, are enzymes which cleave the α-ketosidic bond between a terminal sialic acid residue and an aglycon moiety. The aglycon is usually the penultimate sugar residue of a glyco conjugate or glycoprotein carbohydrate chain. The first sialidase was purified and characterized from the influenza virus and the bacteria *Vibrio cholerae* [Gottschalk, A. (1957). Neuraminidase: The Specific Enzyme of Influenza Virus and *Vibrio cholerae*. *Biochim Biophys Acta.*, 23, pp. 645–646]. Today, sialidases specific for varying ketosidic linkages have been identified in viruses, bacteria, parasites, and mammals. They play a critical role in viral, bacterial, and protozoa biology by mediating metabolism, adherence, and infection, and are important regulators of alternate complement pathway activation, red blood cell destruction, cell growth, cell adhesion, and tumor metastasis in mammalian systems.

Therefore, the development of sialidase inhibitors could lead to a better understanding of these mechanisms. Also, given the wide prevalence and important role of sialidases in microbial infection, it is highly desirable to develop sialidase inhibitors to be used as anti-bacterial and anti-trypanosomal agents.

Though sialidases have long been identified in bacteria, the last twenty years have seen an explosion of bacterial sialidases purified and characterized due to the advance of molecular biological techniques. The explosion has also shed light on sialidase's role in bacterial metabolism, adherence, infection, and pathogenicity. Except for the active site, the bacterial sialidases do not exhibit an amino acid sequence similarity to the viral sialidases. Another characteristic of bacterial sialidases is the presence of non-sialidase related domains in the protein. These domains have other activities or functions which are beneficial to the bacteria. Many bacterial sialidases are membrane anchored, like the viral sialidases, while others are excreted extracellularly by the bacterium. Bacterial sialidases fall into two further subgroups based upon divalent metal requirements. The sialidase subgroup that requires a metal ion is represented by the *Vibrio cholerae* sialidase. The subgroup that does not require a metal ion for activity is represented by several bacterial sialidases, such as *Clostridium perfringens, Clostridium sordelli, Micromonospora viridifaciens,* and *Salmonella typhimurium* among others. In addition to the high degree of sequence homology within the subgroup, the non-metal requiring sialidases also show a large amount of similarity to the N-terminal trans-sialidase domain of the trypanosomal trans-sialidase enzyme. The crystal structure for *Salmonella typhimurium* sialidase has been solved [Crennell, S. J., Garman, E. F., Laver, W. G., Vimr, E. R & Taylor, G. L. (1993), The crystal structure of a bacterial sialidase (from Salmonella typhimurium LT2) shows the same fold as an influenza virus neuraminidase. *Proc Nat Acad of Sci USA.,* 90, pp. 9852–6].

SUMMARY OF THE INVENTION

The present invention provides a method of inhibiting bacterial sialidase comprising administering to a subject an inhibiting effective amount of a compound of formula I:

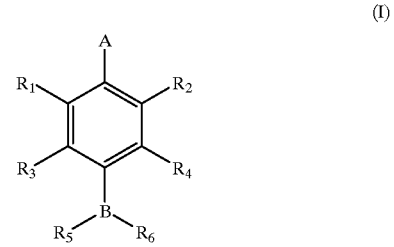

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof The present invention also provides a method of treating a bacterial or trypanosomal infection, comprising administering to a subject a preventative effective amount a compound of formula I wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$ or $COCl_3$; an analog, pharmaceutically acceptable salt, derivative, or mixture thereof In another embodiment, the present invention provides a method of preventing a bacterial or trypanosomal infection, comprising administering to a subject a preventative effective amount a compound of formula I wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH NH2, or halide; $R_5$ is H; and $R_6$ is $COCH_3$, or $COCl_3$; or an analog, pharmaceutically acceptable salt, derivative, or mixture thereof.

In another embodiment, the present invention provides a pharmaceutical composition for inhibiting bacterial sialidase, comprising a pharmaceutically acceptable carrier admixed with an inhibiting effective amount of a compound of formula I wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; an analog, pharmaceutically acceptable salt, derivative, or mixture thereof In another embodiment, the present invention provides a method of making a pharmaceutical composition for inhibiting bacterial sialidase, comprising admixing a pharmaceutically acceptable carrier with an inhibiting effective amount of a compound of formula I wherein A is $CO_2H$, $PO_2H$, or $SO_2H$, B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; an analog, pharmaceutically acceptable salt, derivative, or mixture thereof.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
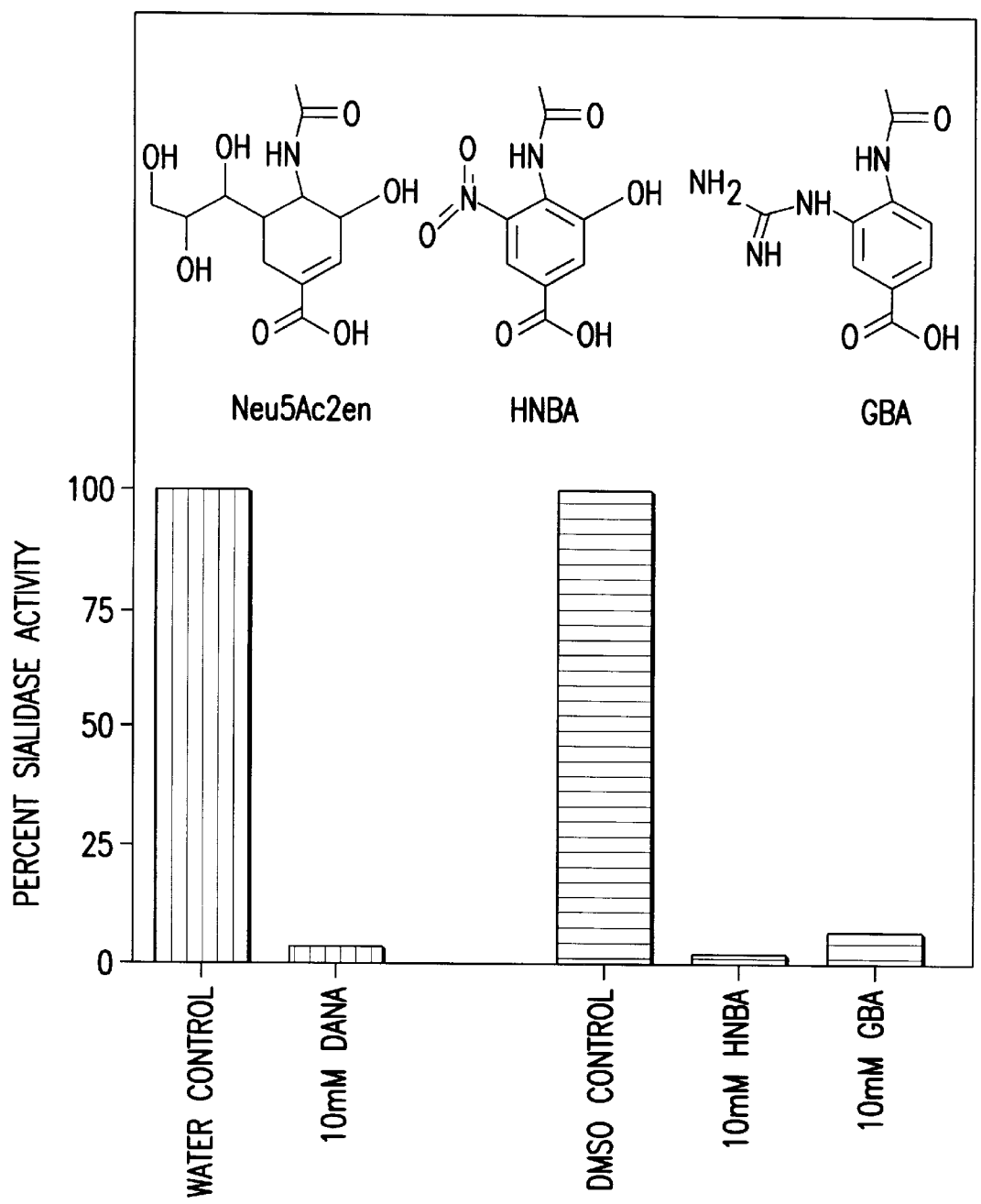
FIG. 1 shows a graph of the inhibitory activity and the chemical structures of Neu5Ac2en, HNBA and GBA.

The present invention provides a method of inhibiting bacterial sialidase comprising administering to a subject an inhibiting effective amount of a compound of formula I:

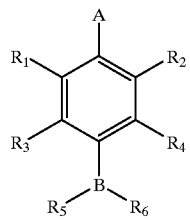

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or allyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof In a preferred embodiment, A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof In yet another preferred embodiment, one of $R_3$ and $R_4$ is OH the other is $NO_2$. In a further preferred embodiment, $R_3$ and $R_4$ is H the other is guanidino. In yet another preferred embodiment, the administering step comprises topical administration.

In another embodiment, the present invention provides a method of treating a bacterial or trypanosomal infection, comprising administering to a subject a preventative effective amount a compound of formula I:

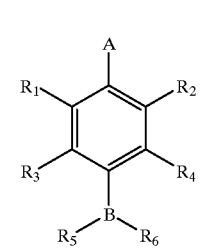

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof In a preferred embodiment, the present invention provides this method A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof. In yet another preferred embodiment, the administering step comprises topical administration.

In yet another embodiment, the present invention provides a method of preventing a bacterial or trypanosomal infection, comprising administering to a subject a preventative effective amount a compound of formula I:

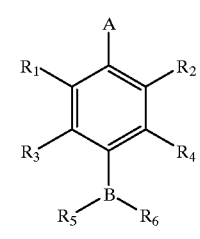

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof In a preferred embodiment, A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof In yet another preferred embodiment, the administering step comprises topical administration.

In another embodiment, the present invention provides, a pharmaceutical composition for inhibiting bacterial sialidase, comprising a pharmaceutically acceptable carrier admixed with an inhibiting effective amount of a compound of formula I:

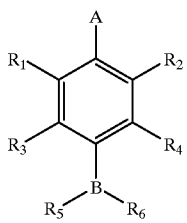

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_5$ is $COCH_3$, or $COCl_3$; or an analog, pharmaceutically acceptable salt, derivative, or mixture thereof In a preferred embodiment, A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof In a further preferred embodiment, the present invention provides a method of making a pharmaceutical composition for inhibiting bacterial sialidase, comprising admixing a pharmaceutically acceptable carrier with an inhibiting effective amount of a compound of formula I:

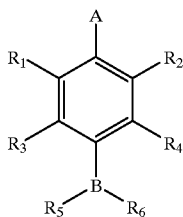

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof In a preferred embodiment, A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof.

A. Design of Benzenoid Inhibitors

2-Deoxy-2,3-didehydro-N-acetylneuraminic acid (DANA) is a known good inhibitor ($K_i=4\times10^{-6}$ M) for influenza A neuramidase [N. R. Taylor and M. von Itzstein, "Molecular Modeling Studies on Ligand Binding to Sialidase from Influenza Virus and the Mechanism of Catalysis," *J Med. Chem.*, 37, 616–624 (1994)]. Evaluation of the interactions between DANA and the sialic acid binding site on neuraminidase reveal that, among the side chains found on the ring of DANA, the carboxylate most strongly associates with the binding site via 4 interactions to three different arginine residues (N2 numbering: Arg 118, 292, and 371). Additionally, the N-acetyl group is the only substituent which occupies a hydrophobic pocket (interactions of methyl with Ile 222 and Trp 178, along with other interactions of the amide carbonyl oxygen with Arg 152 and the amide nitrogen with an ordered water).

For the DANA-neuraminidase complex, the plane of the N-acetyl amide is oriented perpendicular to the plane of, and bisects the O—C═O bond of, the carboxylate. This produces an amide N to Cl distance of 5.51 Å, and an amide O to Cl distance of 6.20 Å.

All known good inhibitors of influenza neuraminidase are carbohydrate derivatives containing the pyran ring, and most are structurally similar to DANA. As drugs, these compounds suffer from potential problems including lack of oral activity, metabolic lability, complicated stereochemistry, difficulty in synthesis and excessive conformational flexibility. The present invention, however, describes simpler non-carbohydrate compounds containing the carboxylate and the N-acetyl groups, or alternative groups that can undergo similar interactions with the binding site, attached to a cyclic backbone "spacer". The cyclic spacer correctly orients the general groups or alternative side chain groupings to provide new classes of neuraminidase inhibitors for further elaboration.

The benzene ring spacer has inherently simple stereochemistry (i.e, no chiral carbons occur at side chain to ring branches), relative conformational rigidity (the predicted positioning of side chain functionality is simplified), relative ease of synthesis, and prospects for oral activity and good metabolic disposition (many useful drugs are based upon benzene).

B. Definitions

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, and the like. Preferred alkyl groups herein contain from 1 to 6, or more preferably 1 to 4, carbon atoms. The term "lower alky" intends an alkyl group of from one to six carbon atoms, preferably from one to four carbon atoms.

The term "alkoxy" as used herein intends an alkyl group bound through a single, terminal ether linkage; that is, an "alkoxy" group may be defined as —OR where R is alkyl as defined above. A "lower alkoxy" group intends an alkoxy group containing from one to six, more preferably from one to four, carbon atoms. Likewise, the terms "alkenoxy" and "alkynoxy" as used herein intend an alkenyl or alkynyl group bound through a single, terminal ether linkage; that is, an "alkenoxy" or "alkynoxy" group may be defined as —OR where R is alkenyl or alkynyl as defined above.

The term "alkenyl" as used herein intends a mono-unsaturated or poly-unsaturated hydrocarbon group of 2 to 24 carbon atoms. Preferred groups within this class contain 2 to 12 carbon atoms. Likewise, the term "alkynyl" as used herein intends a hydrocarbon group of 2 to 24 carbon atoms containing at least one triple bond. Preferred groups within this class contain 2 to 12 carbon atoms.

The term "halide" is used to refer to any halogen including, F, Cl, I, or Br.

The terms "cyclic" and "heterocyclic" refer to rings where, respectively, none or one or more of the carbon atoms have been replaced. For instance, for a "heterocyclic" ring, a carbon in the ring may be preferably substituted with N, O, or S. Such atoms which are substituted are herein called "heteroatoms." One of skill in the art would recognize that other suitable heteroatoms exist.

The term "core ring" is used to refer to the base six-membered ring depicted in general structure I.

The terms "saturation" and "unsaturation" are used to describe whether, between a particular pair of atoms, a single or double bond exists. Single bonds are termed "saturations" and double bonds are termed "unsaturations." One of skill in the art would recognize that triple bonds could also constitute "unsaturations". Furthermore, the terms "saturated" and "partially unsaturated" and "fully unsaturated" are used to refer to the presence or lack of unsaturations in a particular ring. For instance, cyclohexane would be considered a "saturated" compound. On the other hand cyclohexene would be "partially unsaturated" due to the presence of one unsaturation. Finally, benzene is "fully unsaturated" due to the presence of the maximum, three, unsaturations.

The terms "alkanol", "alkenol" and "alkynor", as used herein, refer to the alcohol versions of respective alkanes, alkenes and alkynes. The alcohols may contain one or more OH moieties. Furthermore, the alcohols may be branched or straight and the OH moieties may be present at the terminal carbons or elsewhere along the carbon chain. More than one OH group may be substituted at any particular carbon. Examples of "alkanols" are methanol, ethanol, $CH_3CH(OH)_2$, etc. Examples of alkenols include $CH_2CHOH$, $CH_3CH_2CHOH$, etc. An example of an alkynol is $CH_3CH_2CCOH$. As used in the claims, a substitution of an alkanol implies that one of the hydrogens is removed at the linking atom and that atom is bonded to the entity having the substitution. The same interpretation applies to all other moieties described in this specification where the context requires such interpretation.

As used herein, "subject" is intended to cover humans, mammals and other animals which are susceptible to bacteria in any fashion.

By the term "effective amount" of a compound as provided herein is meant a nontoxic but sufficient amount of the compound to provide the desired utility. For instance, to inhibition of sialidase, the effective amount is the amount which provides clinically meaningful inhibition of sialidase in a subject. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

By "pharmaceutically acceptable" is meant a material that is not biologically or otherwise undesirable, i.e., the material may be administered to an individual along with the selected bicyclic compound without causing any undesirable biological effects or interacting in a deleterious manner with any of the other components of the pharmaceutical composition in which it is contained.

Pharmaceutically acceptable salts are prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., preferably at room temperature. The molar ratio of compounds of general structure I to base used are chosen to provide the ratio desired for any particular salts. For preparing, for example, the ammonium salts of the free acid starting material, the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used. "Salt" is further defined elsewhere herein.

As used herein, and without limitation, the term "analog" is used to refer to any compound which has structural similarity to the compounds of the invention and would be expected, by one skilled in the art, to exhibit the same or similar utility as the claimed compounds.

As used herein, and without limitation, the term "derivative" is used to refer to any compound which has a structure derived from the structure of the compounds of the present invention and whose structure is sufficiently similar to those disclosed herein and based upon that similarity, would be expected, by one skilled in the art, to exhibit the same or similar activities and utilities as the claimed compounds.

C. Synthesis of Benzenoid Inhibitors

Compounds with General Structure I and their pharmaceutically acceptable salts and derivatives, may be prepared using any of several methods known in the art for the synthesis of substituted benzenoid compounds containing analogous structures.

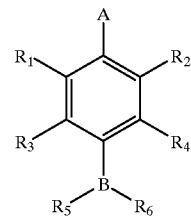

GENERAL STRUCTURE I

To illustrate, potential synthetic approaches for selected examples from General Structure I are summarized in the following two reaction schemes and are representative of the types of procedures to be employed. Table 1 lists some of the compounds successfully synthesized to date.

TABLE 1

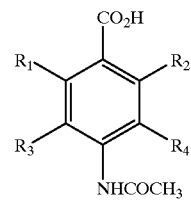

| Compound | $R_1$ | $R_2$ | $R_3$ | $R_4$ |
|---|---|---|---|---|
| 101 | H | H | H | OH |
| 102 | H | H | H | OAc |
| 103 | $NO_2$ | $NO_2$ | H | OH |
| 104 | H | H | $NO_2$ | OAc |
| 105 HNBA | H | H | $NO_2$ | OH |
| 113 GBA | H | H | H | $NHC(NH)NH_2$ |

Table 2 proposes constructing a basic skeleton via formylation ortho to the acetylamino group. This could be accomplished using Friedel-Crafts alkylation with dichloromethyl methyl ether, which has been shown to be a general method for the formylation of numerous substituted benzenes [A. Rieche, H. Gross, and E. Hoft, "Synthesis of Aromatic Aldehydes with Dichloromethyl-Alkyl Ethers," Chem. Ber., 93, 88–94 (1960)]. As illustrated here, the o-formylation of 14 will provide target 24 (via intermediate 23), and the o-formylation of 25–27 will provide precursors 28–30 for the further elaboration to additional targets.

TABLE 2

Scheme for Synthesizing Benzenoid Candidate Inhibitors

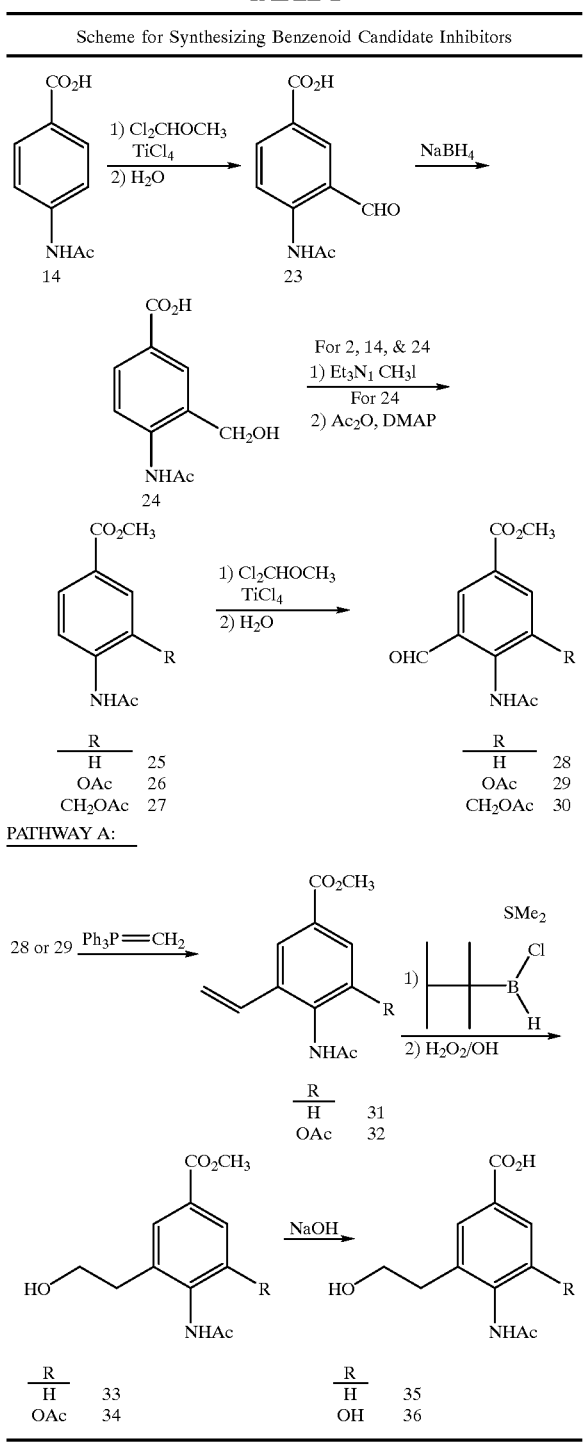

This key o-formylation step occurs early in the proposed syntheses, and if unexpected difficulties are encountered, several alternatives are possible. These include: (a) Other o-formylation methods could be employed, such as the o-formylation of anilines via the rearrangement of azasulfonium salts [P. G. Gassman and H. R. Drewes, "The Ortho Functionalization of Aromatic Amines. Benzylation, Formylation, and Vinylation of Anilines," *J Am. Chem. Soc.,* 100, 7600–7610 (1978)], which has been used for the synthesis of substituted o-acetylamino-benzaldehydes. (b) Since the acetylamino group is a good "directed metalation group" [V. Snieckus, "Directed Ortho Metalation. Tertiary Amide and O-Carbamate Directors in Synthetic Strategies for Polysubstituted Aromatics," *Chem. Rev.,* 90, 879–933 (1990)], it is possible to regioselectively o-lithiate suitable derivatives of 14 and 25–27. Reaction with appropriate electrophiles (epoxides, alkyl halides, aldehydes, etc.) would then provide an entry into desired targets. (c) The o-iodination of protected 14 and 25–27 could be employed in anticipation of a Heck-type coupling reaction [Y. Hatanaka, Y. Ebina, and T. Hiyama, "γ-Selective Cross-Coupling Reaction of Allyltrifluorosilanes: A New Approach to Regiochemnical Control in Allylic Systems," *J Am. Chem. Soc.,* 113, 7075–7076 (1991); K. Nilsson and A. Hallberg, "Synthesis of 1-Propyl-3-(3-Hydroxyphenyl) piperidine by Regiocontrolled Palladium-Catalyzed Acylation," *J Org. Chem.,* 57, 4015–4017 (1992)] to introduce o-substituents. Pathway A describes the proposed elaboration of precursors 28 and 29 to final products. Wittig olefination of the benzaldehydes will provide 31 and 32, and hydroboration-oxidation using thexylchloroborane [H. C. Brown, J. A. Sikorski, S. U. Kulkamni, and H. D. Lee, "Thexylchloroborane-Methyl Sulfide. A Selective Monohydroborating Agent with Exceptional Regioselectivity," *J Org. Chem.,* 45, 4540–4542 (1980)] will provide hydroxyethyl derivatives 33 and 34. Basic hydrolysis of the esters then provides targets 35 and 36.

A similar procedure is proposed in Pathway B (Table 3) for the formation of additional targets. In this procedure 28–30 undergo conversion to iodomethyl derivatives 37–39, which are coupled with two different lithium dialkyl cuprates [G. Posner, "Substitution Reactions Using Organocopper Reagents," *Org. React.,* 22, 253–400 (1975)] to provide 40–44. Glycol formation using N-methylmorpholine-N-oxide and catalytic $OsO_4$ [N. Iwasaw, T. Kato, and K. Narasaka, "A Convenient Method for Dihydroxylation of Olefins by the Combined Use of Osmium Tetroxide and Dihydroxyphenylborane," *Chem. Lett.,* 1721–1724 (1988)], or hydroboration as in Pathway A, followed by basic hydrolysis, then provides the final products 45–53

TABLE 3

Scheme for Synthesizing Benzenoid Candidate Inhibitors

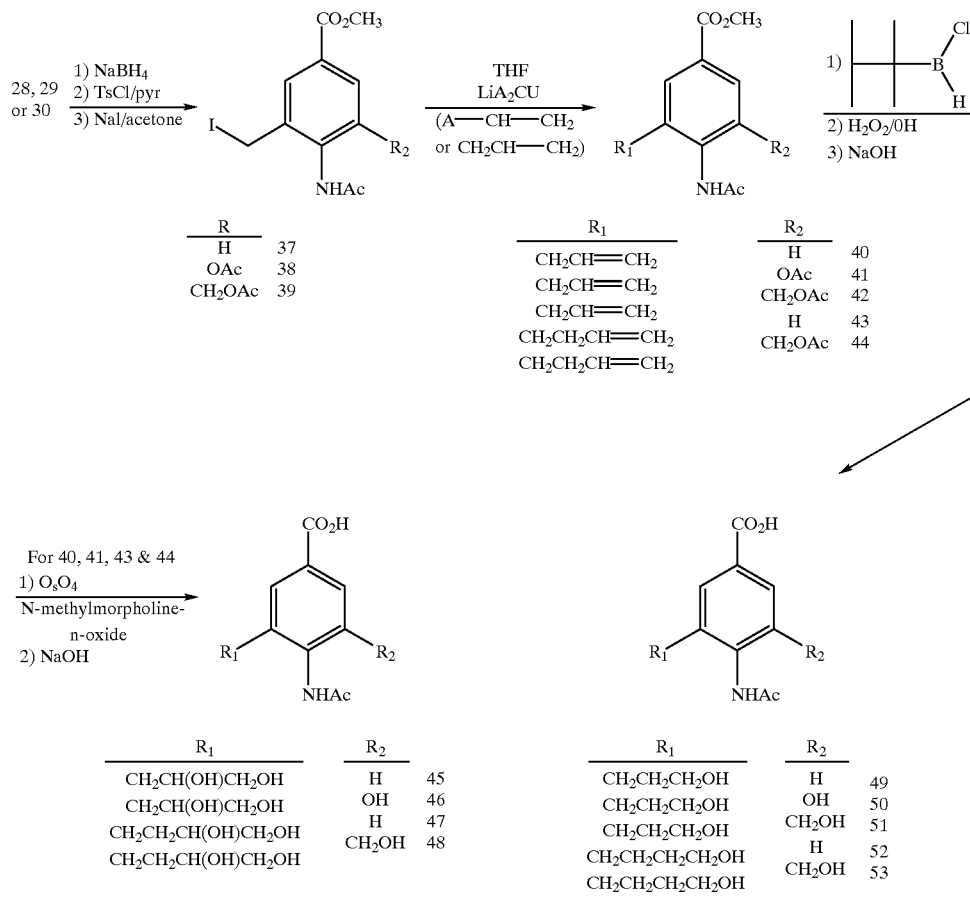

The following detailed examples for methods of preparation are for illustration only, and are not intended to represent a limitation of the invention. The structures of the compounds whose preparations are described below are summarized in Table 1. In all cases synthetic intermediates and products were found to be pure according to standards known to those skilled in the art (such as thin layer chromatography, melting or boiling points, gas chromatography, ion exchange chromatography, and/or high pressure liquid chromatography, elemental analysis, and spectroscopic methods). Furthermore, structures were characterized and fully assigned by spectroscopic methods considered standard practices by those skilled in the art (such as infrared, ultraviolet, and mass spectroscopies, $^1$H and $^{13}$C nuclear magnetic resonance spectroscopy, and/or x-ray crystallography). Selected spectral data are described for intermediates and products.

EXAMPLE 1

The preparations of 4-(acetylanino)-3-hydroxybenzoic acid (101) and 4-(acetylamino)-3-acetoxybenzoic acid (102). The overall reaction scheme is shown in Table 4.

TABLE 4

Reaction Paths and the Chemical Structures of Compounds 13, 102 and 101

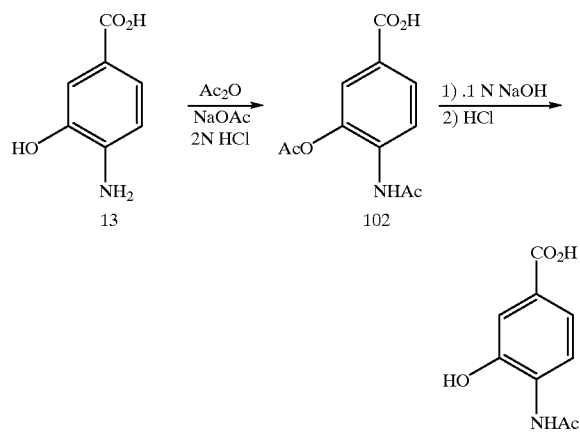

Preparation of 4-(acetylamino)-3-hydroxybenzoic acid (101)

A solution of 102 (100 mg, 0.42 mmol) in 0.1 N NaOH (5 mL) was stirred at room temperature for 30 minutes.

hydroxybenzoic acid, hydrochloride (106). The overall reaction scheme is shown in Table 5.

TABLE 5

Reaction Paths and the Chemical Structures of Compounds 102, 103, 104, 105 and 106

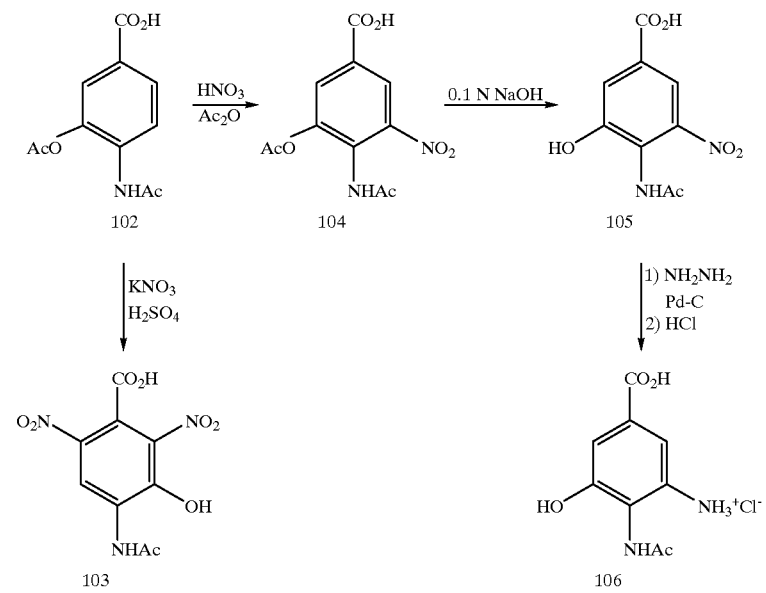

Concentrated HCl was added dropwise to adjust the mixture to pH 2, and this was extracted with ethyl acetate (2×10 mL). The extracts were dried ($Na_2SO_4$), concentrated to dryness on a rotary evaporator, and the solid residue was washed out of the flask with dry hexane and filtered to give 101 (40 mg, 49% yield): mp 249–250° C.

$^1$H NMR (D)MSO-$d_6$) 2.13 (s, 3 H, $COCH_3$), 7.37 (dd, 1 H, aromatic, J=8 & 1.8 Hz), 7.44 (d, 1 H, aromatic, J=1.8 Hz), 8.01 (d, 1 H, aromatic, J=8 Hz), 9.26 (s, 1 H, NH).

Preparation of 3-acetox-4-(acetylamino)benzoic acid (102)

To a stirred solution of commercially available compound 13 (0.50 g, 3.3 mmol) in 2N HCl (10 mL) at 0° C. (ice bath) was added a solution of NaOAc (5.0 g, 61 mmol) in water (25 mL). To this was added $Ac_2O$ (5.4 g, 53 mmol). The mixture was stirred at 0° C. for 5 minutes, and it was then allowed to warm slowly to room temperature as the ice bath melted. After 4 hours a light brown precipitate had formed. This was filtered, washed with water (25 mL), and air-dried to provide 4-(acetylamino)-3-acetoxybenzoic acid (102; 450 mg, 58% yield): mp 219–221° C. ($CH_3OH/H_2O$).

$^1$H NMR (DMSO-$d_6$) 2.17 (s, 3 H, $COCH_3$), 2.35 (s, 3 H, $COCH_3$), 7.69 (d, 1 H, aromatic, J=1.8 Hz), 7.79 (dd, 1 H aromatic, J=7 & 1.8 Hz), 8.17 (d, 1 H, aromatic, J=7 Hz), 9.3 (s, 1 H, NH).

EXAMPLE 2

The preparations of 4-(acetylamino)-3-hydroxy-2,6-dinitrobenzoic acid (103), 3acetoxy-4-(acetylamino)-5-nitrobenzoic acid (104), 4-(acetylamino)-3-hydroxy-5-nitrobenzoic acid (105), and 3-amino-4-(acetylamino)-5-

Preparation of 4-(acetylamino)-3-hydroxy-2,6-dinitrobenzoic acid (103)

3-Acetoxy-4-(acetylamino)benzoic acid (102; 2.00 g, 8.43 mmol) was added gradually to a paste made from concentrated $H_2SO_4$ (8.5 mL) and potassium nitrate (2.22 g, 22.0 mmol) at −10–0° C. The reaction was stirred at 0° C. for 30 minutes, and the syrupy mass was poured onto cracked ice. After standing for one hour a yellow solid separated. This was filtered, washed on the filter with cold water, and air-dried to give 103 (1.60 g, 66.7% yield): mp 199–203° C. (ethyl acetate/hexane).

1H NMR (DMSO-d6) 2.16 (s, 3 H, $NCOCH_3$), 8.73 (s, 1 H, aromatic), 9.72 (s, 1 H, NH).

Preparation of 3-acetoxy-4-(acetylamino)-5-nitrobenzoic acid (104)

Compound 102 (1.00 g, 4.21 mmol) was suspended with stirring in a mixture of $Ac_2O$ (8.33 mL, 8.99 g, 88.2 mmol) and dioxane (6.6 mL). This was cooled to 0° C., and a cold solution of the nitrating mixture made from $Ac_2O$ (3.33 mL, 3.59 g, 35.2 mmol) and concentrated $HNO_3$ (3.33 mL) was slowly added to the mixture containing 102. The reaction mixture was then warmed to 30–35° C. until the reaction was complete as evidenced by TLC. The reaction mixture was poured onto ice/water (100 mL), extracted with EtOAc (4×50 mL), dried ($NaSO_4$), and concentrated to dryness on a rotary evaporator to give crude 104 (1.05 g, 89.9%) as an oil. Trituration with $CHCl_3$ gave a solid: mp 196–201° C. (dioxane/hexane).

1H NMR (CD3OD) 8.42–8.33 (d, J=1.5 Hz, 1 H, aromatic), 8.05–8.12 (d, J=1.5 Hz, 1 H, aromatic), 2.35 (s, 3 H, $OCOCH_3$), 2.13 (s, 3 H, $NCOCH_3$).

Preparation of 4-(acetylamino)-3-hydroxy-5-nitrobenzoic acid (105)

Compound 104 (0.850 g, 3.54 mmol) was dissolved in 0.1N NaOH (80 mL), and the mixture was stirred at room temperature for 4 hours. This was acidified with concentrated HCl (2 mL), diluted with water (20 mL), and extracted with ethyl acetate (3×60 mL). The combined extracts were dried ($Na_2SO_4$) and concentrated on a rotary evaporator to give crystalline 105 (0.712 g, 98.4% yield): mp 256–259° C. (methanol).

$^1$H NMR (DMSO-$d_6$) 10.93 (s, 1H, COOH), 9.90 (s, 1H, NH), 7.79–7.69 (mn, 3 H, aromatic), 2.04 (s, 3 H, $NCOCH_3$).

Preparation of 3-amino-4-(acetylamino)-5-hydroxybenzoic acid, hydrochloride (106)

Compound 105 (100 mg, 0.416 mmol) was dissolved in ethanol (3 mL), and Pd-C (100 mg) was added to it. To this mixture was added hydrazine hydrate (55% hydrazine, 0.10 mL, 55 mg, 1.7 mmol) dropwise. The reaction mixture was heated at reflux for 1 hour. The Pd-C was filtered and the ethanol was concentrated under vacuum to give the free amine of 106 as a pale yellow oil (85 mg, 97% yield). The oil was dissolved in ethanol (3 mL), HCl (gas) was bubbled through the solution for a few minutes, and ether (10 mL) was added. No precipate formed, so the solution was concentrated to dryness to give 106 (100 mg) as the hydrochloride salt: mp 220° C. (dec).

$^1$H NMR ($D_2O$) 7.45–7.40 (m, 2 H, aromatic), 2.22 (s, 3 H, $NCOCH_3$).

EXAMPLE 3

The preparations of 4-(acetylamino)-3-hydroxy-5-nitrobenzoic acid (107), 4-(acetylamino)-3-aminobenzoic acid (108), and 4-(acetylamino)-3-guanidinobenzoic acid (113). The overall reaction scheme is shown in Table 6.

TABLE 6

Reaction Paths and the Chemical Structures of Compounds 14, 107, 108 and 113

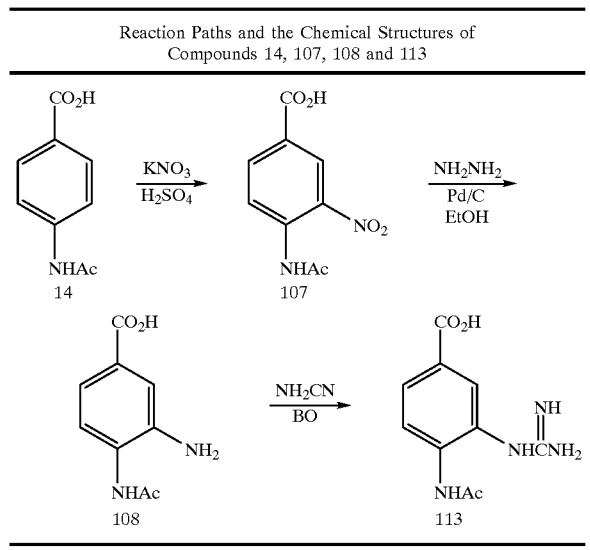

Preparation of 4-(acetylamino)-3-hydroxy-5-nitrobenzoic acid (107)

Commercially available compound 14 (5.00 g, 27.9 mmol) was gradually stirred into a paste prepared by adding finely pulverized potassium nitrate (6.70 g, 66.3 mmol) to concentrated $H_2SO_4$ (30 mL), and the mixture was stirred at −10 to 0° C. in a salt/ice bath for one hour. The syrupy mass was then slowly poured onto cracked ice. After standing for one hour the yellow precipitate was filtered, washed on the filter with cold water, and air-dried to give 107 (5.27 g, 84.3% yield): mp 215–20° C (ethanol). The literature (Verma and Khan, 1978) reports mp 218–220° C.

$^1$H NMR (DMSO-d6) 10.57 (s, 1 H, COOH), 8.36 (s, 1 H, aromatic), 8.2 (d, J=8.5 Hz, 1 H, aromatic), 7.82 (d, J=8.5 Hz, 1H, aromatic), 2.11 (s, 3 H, $COCH_3$).

Preparation of 4-(acetylamino)-3-aminobenzoic acid hydrochloride (108)

To a stirred mixture of 107 (1.00 g, 4.46 mmol) and 10% Pd-C (1.0 g) in ethanol (10 mL) and 5% HCl (1.2 mL) was added dropwise hydrazine hydrate (55% hydrazine, 1.0 mL, 17 mmol). The mixture was stirred at room temperature for 1 hour, the catalyst was filtered, and the filtrate was concentrated under reduced pressure. Compound 108 (0.875 g, 100%) was obtained as a white solid residue: mp 220–223° C. (methanol/hexane). A literature reference (Ellis and Jones, 1974) did not report the mp.

$^1$H NMR ($CD_3OD$) 7.49–7.29 (m, 2 H, aromatic), 7.20–7.12 (m, 1 H, aromatic), 2.16 (s, 3 H, $COCH_3$).

Preparation of 4-(acetylamino)-3-guanidinobenzoic acid (113)

A mixture of 108 (100 mg, 0.43 mmol) and cyanamide (27 mg, 0.65 mmol) was mixed and heated at 85–100 C. with stirring for 15 minutes. The liquid mass was cooled to room temperature, dissolved in hot water (0.7 mL), and acidified with 1–2 drops of conc. HCl. The thick solid which separated was filtered and dried to give crude 113 (160 mg). This was recrystallized from 5% HCl to give the pure hydrochloride salt of 113 (50 mg, 52%): mp 284–287 C.

$^1$H NMR (TFA) 2.50 (s, 3 H, $NCOCH_3$), 6.50 (bs, 4 H, $C(NH_2)_2^+$), 7.55 (d, 1 H, aromatic), 8.25–8.44 (m, 3 H, aromatic & $NHC(NH_2)_2^+$), 9.30 (bs, 1 H, NHAc).

D. Structure-Based Solutions

Structure-based drug design developed out of the fact that potential drugs had previously been discovered only serendipitously or by the use of extensive screening assays. To improve the therapeutic properties of existing compounds, traditional methods such as qualitative structure-activity relationship (QSAR) analysis have been used. However, to clearly understand the multitude of forces which affect a drug's biological activity (or lack thereof), the three-dimensional structure of the native target, or more preferably, the complex between the target and the drug, must be solved. In many cases, the structure of a particular drug-target complex can provide an immediate explanation to long-standing and perplexing biochemical questions of function and activity. Hence, the method of structure-based drug design, which uses the three-dimensional structure of a selected target or target-drug complex to guide the design new compounds. By starting with the structure of the target, the structure-based drug design protocol circumvents the problems and limitations associated with traditional methods of drug development. New compounds that show high specificity and affinity for the target site can be developed using the chemical and geometric structure of target site at high resolution and structure-based design [Ealick, S. E., Babu, Y. S., Bugg, C. E., Erion, M. D., Guida, W. C., Montgomery, J. A. & Secrist III, J. A. (1991). Application of crystallographic and modeling methods in the design of purine nucleoside phosphorylase inhibitors. *Proceedings of the National Academy of Science, USA* 88, 11540–44].

As recently as 1987, to develop a marketable new drug by traditional methods cost an estimated $231 million and required 12 years. The enormous number of potential compounds that are chemically synthesized contributes to the high cost of traditional development methods. Also, traditional methods are inefficient because many synthesized compounds are eventually rejected due to poor activity or adverse side effects. In comparison, the time requirement and costs of developing a drug using structure-based design methods are much lower. In this newer approach, the candidate drugs are modeled into the three-dimensional structure of the target before synthesis and only sterically and chemically compatible structures are synthesized. The screening process further increases the likelihood that the candidate compounds will bind to the active site. The current invention targets bacterial sialidase.

E. Structure-Based Design of Anti-Bacterial and Anti-Trypanosomal Compounds

Bacterial sialidases have been implicated and correlated with several disease such as, inter alia, dental caries, bacterial vaginosis, middle ear effusions, arteritis, acne, and acute streptococcal infection. Though many antibiotics are available to treat bacterial infections, they are often expensive or have significant side effects for the subject. The bactericidal agents of the present invention, however, do not suffer from the expense or potential side effects. Also, basic scientific research into the role of sialidases in bacterial biology and infection would benefit from the elucidation of bacterial-specific sialidase inhibitors.

In addition to bacteria, there are unique enzymes found only in trypanosomes which are also ideal targets for developing anti-trypanosomal therapeutics. One trypanosomal target is the cell-surface anchored trans-sialidase enzyme, which transfers a terminal sialic acid from a donor sialoglycoconjugate to a terminal β-1,4-linked galactose acceptor. The trans-sialidase enzyme found in the protozoa Trypanosomatidae family is believed to play a important role in several human diseases, such as Chagas' disease (*Trypanosoma cruzi*) and African sleeping disease (*Trypanosoma gambiense* and *T. rhodesiense*), as well as, in several animal trypanosomiasis (*Trypanosoma brucei*, and potentially *T. evansi, T. congolense*, and *T. vivax*). It is estimated that there are several million cases of Chagas' disease in Central and South America, as well as several millions cases of African sleeping sickness in sub-Sahara Africa. Every year, several thousand new cases of Chagas' disease and African sleeping sickness occur. The rate of trypanosomiasis in the animal kingdom, which can have serious health and economic implications, is difficult to quantify but is potentially several million cases. Though previous drugs have been developed to treat the trypanosomal infections in humans and animals, they are either relatively toxic to the host or the target trypanosome strains have developed a drug resistance mechanism. Inhibitors of trans-sialidase promise to be effective anti-trypanosomal agents because the trypanosomal trans-sialidase enzyme has been shown to be required for infection in humans, as well as, in animals (limited data) [de Titto, E. H. & Araujo, F. G. (1987). Mechanism of cell invasion by *Trypanosoma cruzi*: importance of sialidase activity. *Acta Trop.* (Basel), 44, pp. 273–82; Ming, M., Chuenkova, M., Ortega-Barria, E. & Pereira, M. E. (1993). Mediation of *Trypanosoma cruzi* invasion by sialic acid on the host cell and trans-sialidase on the trypanosome. *Mol Biochem Parasitol.,* 59, pp. 243–52; and Prioli, R. P., Mejia, J. S. & Pereira, M. E. (1991). On the interaction of *Trypanosoma cruzi* neuraminidase and human lipoproteins. *Eur J Epidemiol.,* 7, pp. 344–8]. The structure-based design of the present invention has led to specific drugs for the trans-sialidase active site. Based on those structures, the drugs of the present invention have a reduced possibility of harming the host or eliciting a drug resistance due to mutation of the target site.

F. *Salmonella typhimurium* Sialidase Activity

The sialidase gene, nanH, from the enteric Gram-negative bacterium *S. typhimurium* has been cloned and the expressed bacterial sialidase has been well characterized [Hoyer, L. L., Roggentin, P., Schauer, R. & Vimr, E. R. (1991). Purification and properties of cloned *Salmonella typhimurium* LT2 sialidase with virus-typical kinetic preference for sialyl alpha 2→3 linkages. *J Biochem.,* 110, pp. 462–7; Hoyer, L. L., Hamilton, A. C., Steenbergen, S. M. & Vimr, E. R. (1992). Cloning, sequencing and distribution of the *Salmonella typhimurium* LT2 sialidase gene, nanH, provides evidence for interspecies gene transfer. *Molecular Microbiology* 6(7), 873–84]. No significant differences were detected in the expressed enzyme as compared to the wild type sialidase, except in the wild type strain, the sialidase accounts for <1% of the total protein. The *S. typhimurium* sialidase has a 260-fold cleavage preference for α2→3 over α2→6 linked sialic acids. In addition, the *S. typhimurium* sialidase has a high enzymatic activity for ganglioside and mucin substrates containing terminal sialic acids. The *S. typhimurium* sialidase does not efficiently recognize α2→8 or α2–9 linked sialic acids and therefore shows little cleavage activity for colominic acid, which is a homopolymer of sialic acid, or Group C polysaccharides.

Like the influenza virus sialidase, the *S. typhimurium* sialidase is active over a broad pH range of pH 5.5–7.0, but unlike viral sialidase, the bacterial sialidase does not require divalent metal ions for activity. Using 4-methylumbelliferyl-a-D-N-acetylneuraminic acid (MUN) as the substrate, the *S. typhimurium* sialidase displays a $K_m=2.5\times10^{-4}$ M, and a turnover number $=2,700$ sec$^{-1}$. The dehydro analog of sialic acid, Neu5Ac2en, inhibits *S. typhimurium* sialidase with a $K_i=0.38$ mM. As compared to influenza virus sialidase, high levels of the cleavage product, Neu5Ac, do not inhibit the bacterial sialidase.

G. *Salmonella tphimurium* Sialidase Structure

The *S. typhimurium* sialidase has a molecular weight of 41 kDa and a pI≧9. As stated above, the three-dimensional structure of *S. typhimurium* was determined using x-ray crystallography [Crennell et al., 1993]. The structure was solved to 2.0 Å by the multiple isomorphic replacement method and refined to a crystallographic R-factor of 18.9%. Like influenza virus sialidase, the *S. typhimurium* sialidase is folded into a left-handed propeller motif consisting of six, four-stranded antiparallel β-sheets. The length of the β-strands and the loops connecting the β-strands differs markedly from the viral sialidase structure. One disulfide bond is observed in the *S. typhimurium* sialidase which links the first and second β-sheets.

H. Trypanosomal Trans-sialidase

The atomic structure of the N-terminal trans-sialidase domain of the trypanosomal trans-sialidase protein has not been solved. But the trypanosomal trans-sialidase N-terminal domain has a high sequence homology to the *S. typhimurium* sialidase [Pereira, M. E., Mejia, J. S., Ortega-Barria, E., Matzllevich, D. & Prioli, R. P. (1991). The Trypanosoma cruzi neuraminidase contains sequences similar to bacterial neuraminidases, YWTD repeats of the low density lipoprotein receptor, and type III modules of fibronectin. *J Exp Med.,* 174, pp. 179–91]. Using the sequence alignment of the trypanosomal trans-sialidase to the bacterial sialidase and using the *S. typhimurium* sialidase crystal structure, a three-dimensional model of the trans-sialidase active site was constructed.

The amino acid sequence for trans-sialidase determined by Pereira et al (1991) was compared to the sialidases isolated from the bacteria *Clostridium perfringens* and *Salmonella typhimurium*. The GCG package [Program Manual for the Wisconsin Package, Version 8, September 1994, Genetics Computer Group, Madison, Wis.] of alignment programs was used to align the three sialidase sequences. The protein database entries used were styneur.pep (*S. typhimurium*) and cfsiali.pep (*C. perfringens*). The inclusion of other bacterial sialidase sequences in addition to the Salmonella and Clostridium sequences did not improve the overall fit of the of the bacterial enzymes to the trans-sialidase. The major features of the proposed bacterial sialidase-trypanosomal trans-sialidase sequence alignment are as follows.

First, the sequence alignment did not predict a trans-sialidase partner for Arg 37 in *S. typhimurium* sialidase sequence. This arginine is part of the arginine triad found in all influenza and bacterial sialidases to date and is required to bind the carboxylate group of the substrate, sialic acid. Second, three cysteine residues in the bacterial sialidase are replaced by non-cysteine residues in the predicted trans-sialidase alignment. The three residues affected are Cys 103, Cys 225, and Cys 344 (*S. typhimurium* numbering). Third, two non-cysteine residues in the bacterial sialidase are predicted to be cysteine residues in the trypanosomal trans-sialidase. The residues in *S. typhimurium* which change to cysteines in the trans-sialidase are Lys 94 and Gly 229. Note, neither the Lys or Gly residues are conserved in the *C. perfringens* sialidase.

On the basis of the proposed sequence alignment, the active site residues of the Salmonella structure were replaced with the trans-sialidase residues identified from the sequence alignment. The program SAM in the FRODO package was used the construct the trans-sialidase homology model. SAM builds the new residues using the original residue atom positions of the *S. typhimurium* crystal structure. One round of limited energy minimization was applied to the trans-sialidase homology model.

I. In Vitro Testing of Benzoic Acid Inhibitors Against Bacterial Sialidase

Aside from moderate inhibitory activity, carbohydrate based inhibitors of sialidase such as Neu5Ac2en suffer as potential therapeutics due to the unfavorable economics and difficulty of manufacturing large scale amounts of the compounds. Benzoic acid based sialidase inhibitors are chemically easier and cheaper to synthesize.

In addition, there are numerous common synthetic routes available to selectively modify a benzene ring with different chemical functional groups. Furthermore, substitution of a benzene ring for the sugar ring of Neu5Ac2en does not dramatically affect inhibitory activity. Previous studies have shown that the sugar ring of the carbohydrate-based inhibitors does not interact directly with the protein active site and only serves as a scaffolding to direct the placement of the inhibitor function groups. The similar geometry and size of a benzene ring to the carbohydrate ring of Neu5Ac2en supports the hypothesis that a benzene ring could act as a scaffolding element for inhibitor functional groups and, therefore, benzoic acid based compounds could inhibit sialidase activity.

Two benzoic acid derivatives, 4-acetylamino-3-hydroxyl-5-nitro-benzoic acid (HNBA) and 4-acetylaniino-3-guanidino-benzoic acid (GBA), which are, respectively, millimolar and micromolar inhibitors of influenza virus sialidase, were tested for inhibitory activity against bacterial sialidase (*Micromonospora viridifaciens*) using a fluorescence assay and the substrate 4-methylumbelliferyl-a-D-N-acetylneuraminic acid (MUN). FIG. 1 shows the relative inhibition activity for the compounds HNBA and GBA versus Neu5Ac2en (bacterial sialidase $K_1 \times 10^6$M) determined for *M. viridifaciens* bacterial sialidase.

The inhibition activities were determined using a modified standard fluorometric assay employing 4-methylumbelliferyl-a-D-N-acetylneuraminic acid (MW as the substrate. Since the benzoic acid compounds have a low solubility in water, a 100 mM stock solution of the benzoic acid compounds was prepared in the organic solvent dimethyl sulfoxide (DMSO). An appropriate amount of the DMSO stock solution was added to the reaction mixture which contained a final concentration of 10 mM inhibitor, 0.1 mM MUN, 50 mM NaAc (pH 6.0), 0.075 mM $CaCl_2$, 0.240 mM $MgCl_2$, 0.045 mM NaCl, and bacterial sialidase (diluted to give a linear response range in the fluorometer). Following addition of MUN, the sample was incubated at 37° C. for 15 minutes. The reaction was stopped by the addition of 25 mM HEPES (pH 11.0). The amount of fluorescent product generated in the reaction was measured using an excitement wavelength of 365 nm and emission wavelength of 450 nm.

The inhibition activity of Neu5Ac2en was standardized against a background control containing only water and no Neu5Ac2en. Likewise, the inhibition activity of the benzoic acid compounds was standardized against a control containing only DMSO to negate the potential inhibition effects of DMSO on bacterial sialidase. Due to standardization, the inhibition activities of Neu5Ac2en and the benzoic acid inhibitors are reported as percent inhibition values. The percent inhibition of Neu5Ac2en serves as a positive control for inhibition by the benzoic acid compounds.

J. Modeling of Inhibitors into Bacterial Sialidase

The compounds, HNBA and GBA, are potent inhibitors of both type A and B influenza virus sialidase. The $IC_{50}$ for HNBA inhibition of influenza virus sialidase is approximately 10 mM, similar to the Neu5Ac2en $IC_{50}$ for influenza virus sialidase inhibition. Based on the inhibition assay results, HNBA and GBA also inhibited bacterial sialidase with efficiencies similar to Neu5Ac2en.

Initial modeling of the benzoic acid lead compounds into the bacterial sialidase was guided by the crystal structure of the Neu5Ac2en-bacterial sialidase complex. The placement of the benzoic acid inhibitors into the bacterial active site by superposition onto the Neu5Ac2en position did not disturb the overall geometry of the active site, as evidenced by the low root-mean-square deviation between the energy minimized benzoic acid and Neu5Ac2en bacterial sialidase complexes.

In the bacterial sialidase, superposition of GBA to align its guanidinium group to the Neu5Ac2en O4 hydroxyl group, which will mimic the 4-guanidino-Neu5Ac2en binding mode, is not possible due to steric conflicts with residues Arg 56 and Asp 100 in bacterial sialidase. This steric interference in the Neu5Ac2en O4 pocket also explains the inhibition selectivity of 4-guanidino-Neu5Ac2en for influenza virus sialidase versus bacterial sialidases. The rotation of the GBA ring resulting from energy minimization may be due to the lack of an hydroxyl group at the C5 position in GBA, which would bind in the Neu5Ac2en O4 hydroxyl site.

K. Modeling of Inhibitor-Bacterial Sialidase Complexes

The structure of a prototypical bacterial sialidase from *S. typhimurium* complexed with the inhibitor Neu5Ac2en by

Figure 2:
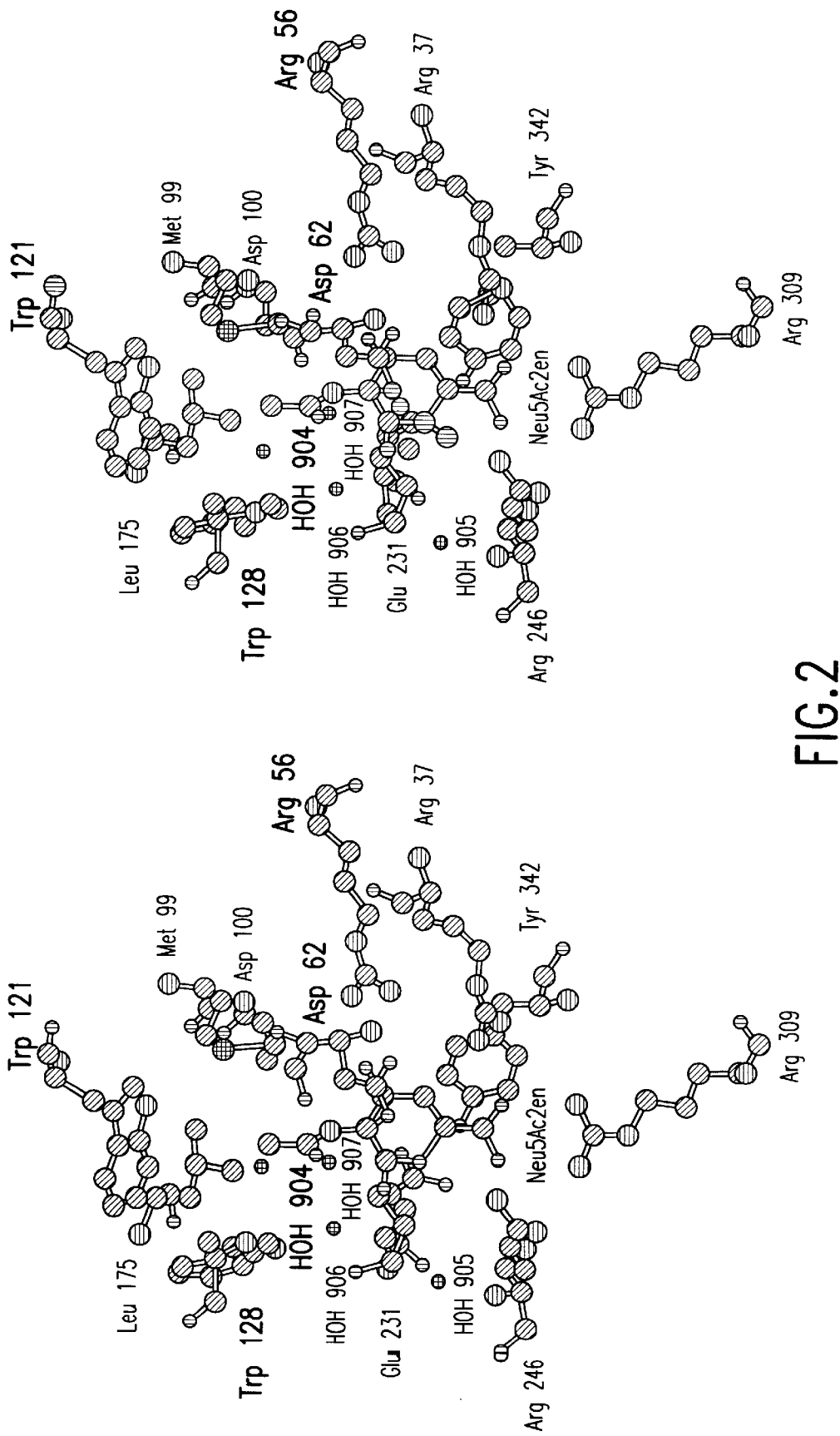
FIG. 2a shows a stereopair view of energy minimized Neu5Ac2en in the sialidase binding site.

Crennell et al. was used to position the benzoic acid inhibitors BNBA and GBA into the bacterial sialidase active site. The interactions between Neu5Ac2en and the active site of the bacterial sialidase are shown in FIG. 2a.

Figure 3A:
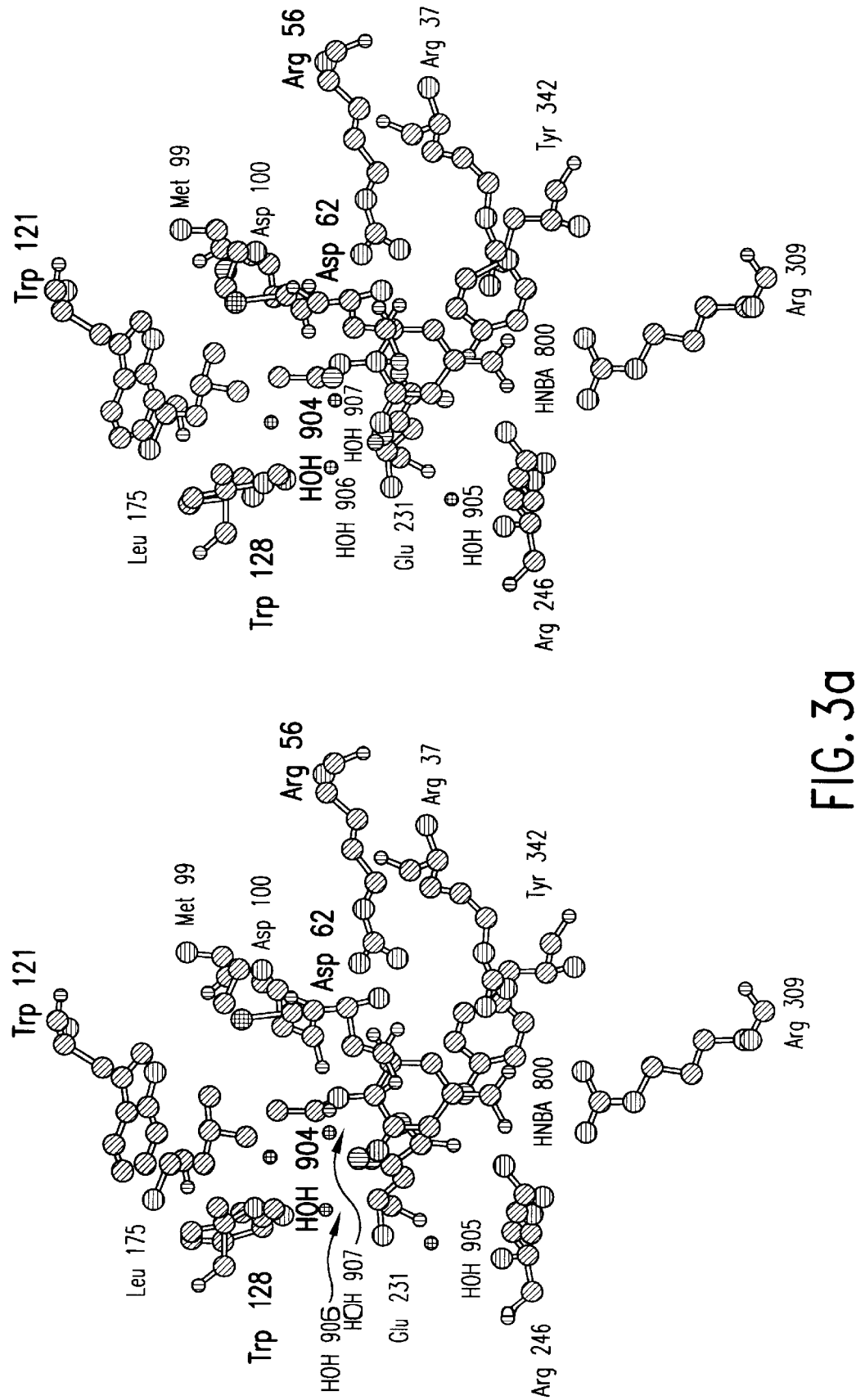
FIG. 3a shows a stereopair view of energy minimized HNBA in the sialidase binding site.

To model the HNBA-bacterial sialidase complex, the C1, O3, and atoms of HNBA were superimposed onto the C2, O4, C6 atoms of Neu5using at least-squares approach. The superposition aligns the C1 carboxylate, C3 hydroxyl, and C4 acetylamino groups of HNBA with the C2 carboxylate, O4 hydroxyl, and C4 acetylamino groups of Neu5Ac2en and preserves the important interactions of these groups with the bacterial sialidase active site residues in the HNBA-bacterial sialidase modeled complex. See FIG. 3a.

Figure 3B:
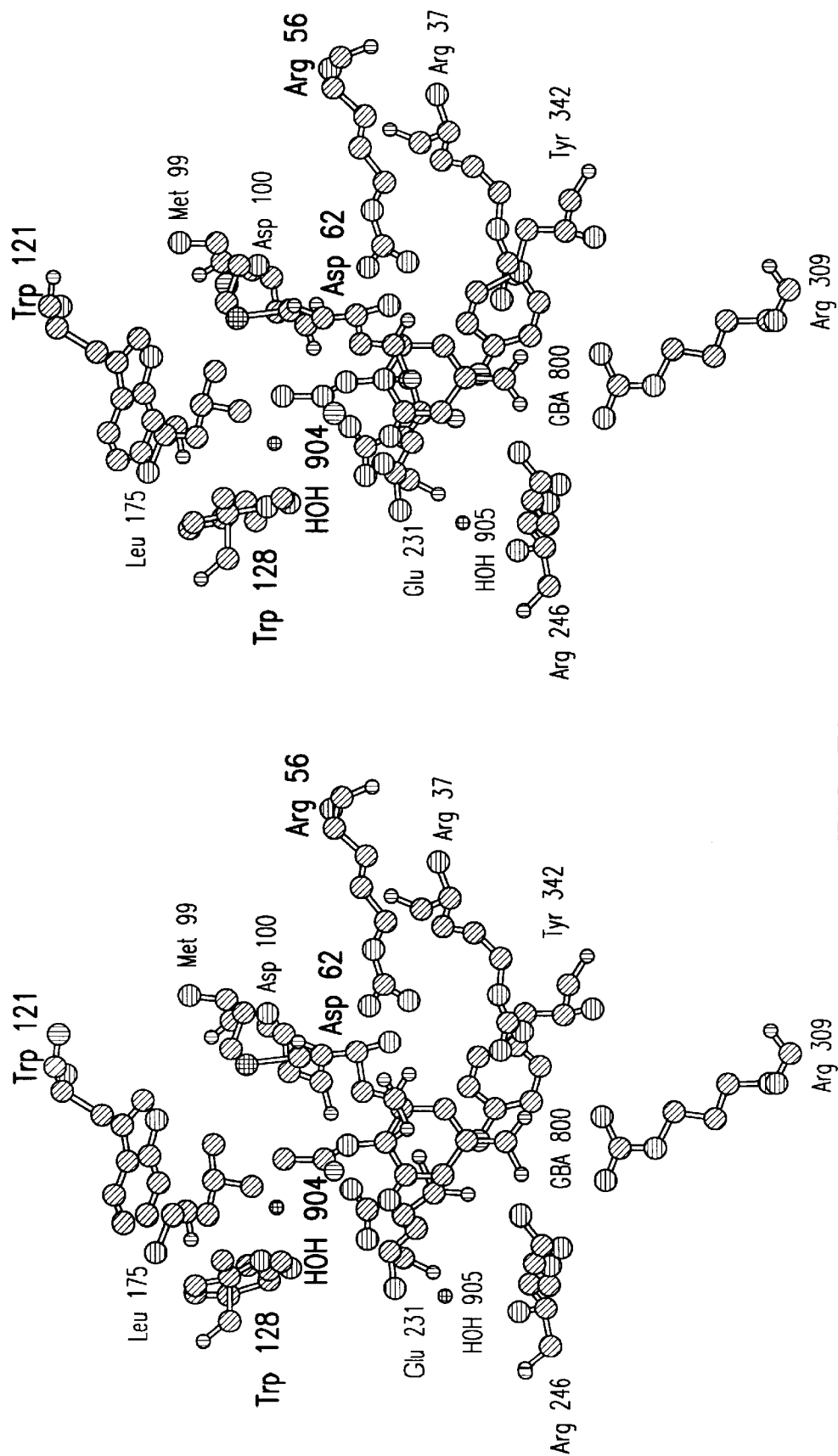
FIG. 3b shows a stereopair view of energy minimized GBA in the sialidase binding site.

The GBA-bacterial sialidase complex was modeled by a least squares superposition of the C1, N3, and C5 atoms of GBA onto the C2, C7, and C3 atoms of Neu5Ac2en. See FIG. 3b. The superposition aligns the GBA guanidinium group to the Neu5Ac2en glycerol group in the bacterial sialidase active site. This orientation corresponds to the binding mode observed in the GBA influenza virus type A N2 sialidase complex. Following the initial least squares superposition, the guanidinium sidegroup of GBA was manually rotated into the $N3^+$ binding site A identified in the GRID map analysis on a graphics display using the program FRODO.

All of the water molecules identified in the Neu5Ac2en-bacterial sialidase crystal structure were included in the HNBA-bacterial sialidase model. The criteria for retaining the waters in the HNBA-bacterial sialidase complex was that none of the water molecules were sterically excluded by the presence of the HNBA inhibitor and all of the water molecules possessed potential hydrogen bonding partners. In the GBA-bacterial sialidase, two of the water molecules in the Neu5Ac2en-bacterial complex, HOH 906 and HOH 907, were excluded due to steric overlap with the GBA guanidino group.

The HNBA and GBA bacterial sialidase complexes were energy minimized using a conjugate gradient protocol within the program X-PLOR to relieve steric conflicts that may have resulted from the Neu5Ac2en superposition. A harmonic constraint of 500 kcal/mol was placed on atoms more than 10 Å distant from the benzoic acid compound, while those atoms within a 10 Å radius of the benzoic acid compound had no harmonic constraints. The active site geometry in the energy minimized benzoic acid-bacterial sialidase complexes was almost identical to that observed in the energy minimized Neu5Ac2en-bacterial sialidase complex. Energy minimization of the HNBA-bacterial sialidase complex did not significantly alter the orientation of HNBA in the bacterial sialidase active site. Surprisingly, energy minimization of the GBA-bacterial sialidase complex changed the orientation of GBA in the bacterial sialidase active site when compared to the starting position (Neu5Ac2en least squares superposition). In the energy minimized GBA-bacterial sialidase complex, the benzene ring of GBA is rotated approximately 20° around the inhibitor carboxylate-acetylamino axis. The rotation places the GBA guanidino group closer to the $N3^+$ binding site and tilts the benzene ring C5 and C6 atoms away from the active site floor. Despite the tilt in the GBA benzene ring, no change in orientation was observed for the GBA carboxylate and N-acetylamino groups in the energy minimized GBA-bacterial sialidase complex when compared to the energy minimized HNBA-bacterial sialidase complex. In addition, the active site residues in both of the energy minimized benzoic acid-bacterial sialidase complexes adopt conformations which are analogous to the active site residues of the energy minimized Neu5Ac2en-bacterial sialidase. The root-mean-square (rms) deviation for sialidase atoms within the 10 Å radius between the energy minimized Neu5Ac2en and HNBA-bacterial sialidase complexes, is 0.05 Å, between the minimized Neu5Ac2en and GBA-bacterial sialidase complexes, 0.07 Å.

As used herein, the term "salt" refers to the cation, such as $Li^+$, $K^+$, $Na^+$, $Ca^{2+}$, $Mg^{2+}$, $Al^{3+}$ etc., which corresponds to the $COO^-$ group of the inhibitors. Sodium salts are often preferable for pharmaceutical compositions. One of ordinary skill in the art would recognize that the fundamental utility of the compounds is not dependent upon the identity of the particular cation. As shown, $H^+$ is also a suitable cation.

The program DELPHI calculates the electrostatic potential of macromolecular systems using a finite difference solution to the non-linear Poisson-Boltzmann equation [Gilson, M K, & Honig, B, Calculation of the total electrostatic energy of a macromolecular system; solvation energies, binding energies, and conformational analysis. *Proteins: structure, function and genetics,* 4, pp. 7–18 (1988)]. For a given macromolecular inhibitor-protein complex, DELPHI can be used to calculate the total electrostatic energy of the system. For the modeled complexes, the electrostatic contribution to the free energy change upon complex formation, $\Delta G_{el}$, was derived from the total electrostatic energies of three inhibitor complexes: E1, the electrostatic energy of the complex when charges are present only on the protein residues; E2, the electrostatic energy of the complex when charges are present only on the inhibitor residues; and E3, the electrostatic energy of the complex when charges are present on both the protein and inhibitor residues. The free energy change resulting from electrostatic interactions is therefore: $\Delta G_{el} = E_1 - (E_2 + E_3)$. Because the binding of inhibitors to the bacterial active site is dominated by electrostatic interactions and due the inherent complexity of hydrophobic interactions, the contribution of the hydrophobic effect was not explicitly included in the DELPHI calculation. However, the contribution of the hydrophobic effect to the free energy of complex formation for compounds within a single class, which have a similar functional groups and chemical properties, is roughly on the same order of magnitude. Therefore, exclusion of the hydrophobic contribution to the calculated free energy of complex formation should not change the relative ranking of a series of compounds within any single class.

For each of the modeled complexes, the electrostatic contribution to the change in free energy of complex formation was calculated using a protein/inhibitor dielectric constant of 4, a solvent dielectric constant of 80, an ionic strength of 0.145 M, and a focusing protocol of 30→90% fill. Table 7 presents the calculated free energies of complex formation for the sialidase complexes, as well as, the calculated free energies of complex formation for the benzoic acid-bacterial sialidase complexes.

TABLE 7

DELPHI electrostatic energies of complex formation for HNBA and GBA when complexed to bacterial sialidase from *Salmonella typhimurium.*

| Data Set | $E_1$ (kT) | $E_2$ (kT) | $E_3$ (kT) | $\Delta G_{el}$ (kT) | $\Delta G_{el}$ (kcal/mol) | $\Delta(\Delta G)$† (kcal/mol) |
|---|---|---|---|---|---|---|
| GBA | 29341.89 | 99.49 | 29388.96 | −52.42 | −31.09 | −12.87 |
| HNBA | 29438.42 | 107.24 | 29514.95 | −30.71 | −18.21 | 0.00 |

\$\Delta(\Delta G) = \Delta G_{el}(i) - \Delta G_{el}(HNBA)$, where $i$ is any inhibitor.

The partial charges assigned to the compounds in the DELPHI calculation were determined using the semiemperical program MOPAC v6.0 and the coordinates of the final energy minimized inhibitor compound when complexed to *S. typhimurium*. The DELPHI electrostatic energies were calculated using a focusing protocol comprised of three stages of the percent fill: 30%, 60%, and 90%. Using 90% fill in the final stage gave a step size of 1.04 Å. The following parameters were used for all DELPHI calculations: protein dielectric, $e_p$=4, solvent dielectric, $e_s$=80, ionic strength=0.145, linear iterations=1000, and non-linear iterations =3000. Unless otherwise stated, the DELPHI default values were used for all other parameters in the electrostatic free energy calculations.

L. Comparison of Influenza Virus and Bacterial Sialidase Active Sites

As with influenza virus sialidases, the bacterial sialidase active site from *S. typhimurium* also contains an arginine triad (Arg 37, Arg 246, and Arg 309), which binds the carboxylate moiety of sialic acid; a hydrophobic pocket, which accommodates the methyl group of the substrate N-acetylamino moiety; and a tyrosine residue (Tyr 342) located beneath the substrate pocket. Though functionally similar, the residues which compose the hydrophobic pocket differ between the bacterial and viral active sites. The bacterial hydrophobic binding site is composed of two tryptophans (Trp 121, Trp 128), one methionine (Met 99), and one leucine (Leu 175), where as the viral hydrophobic pocket contains just one tyrosine (which is analogous in position to Trp 128 of *S. typhimurium*), one isoleucine and one arginine sidechain. In addition, several other features can be used to distinguish the *S. typhimurium* bacterial active site from its counterpart in the influenza virus sialidase. For example, there are several significant differences in the active site residues which form the binding pockets for the O4 hydroxyl and glycerol groups of sialic acid. In the bacterial enzyme, an arginine and an aspartic acid residue (Arg 56 and Asp 100 in *S. typhimurium* ), which the viral sialidase does not contain, form strong hydrogen bonds to the O4 atom of the bound sialic acid. The presence of these residues in the bacterial active site also prevent binding of sialic acid analogs modified at the O4 position with large, bulky groups. At the glycerol binding pocket, the bacterial enzyme is lacking a glutamic residue (Glu 275) found in the influenza virus enzyme which provides two hydrogen bonds to the glycerol O8 and O9 atoms of the bound sialic acid. In addition, in the glycerol pocket found in the bacterial sialidase is much larger and broader than the glycerol pocket of influenza virus sialidase due to the alternate orientation of a loop in the bacterial sialidase. In the bacterial enzyme, the loop, comprised of residues 196–205, points away from the active site to create a wide, shallow glycerol binding pocket. The analogous loop in the influenza virus sialidase points toward the active site and effectively limits the size of the pocket to inhibitor sidegroups no longer than glycerol.

M. Biological Significance

Bacterial and trypanosomal infections of humans and livestock can result in serious medical complications and economic loss. Though anti-biotics are available for the treatment of bacterial infections, inhibitors of bacterial sialidase may be medically useful where sialidase activity has been correlated with severe bacterial infection pathology.

N. Modes of Administration

As used herein, the effective amount of a compound of the invention required for use in the methods described herein will vary not only with the particular compound selected but also with the mode of administration, the nature of the condition in the subject, and the age and health of the subject. The exact dosage will ultimately be determined by a physician or other person skilled in the art. However, a suitable systemic dose will generally range from about 0.01 to about 200 mg/kg of bodyweight per day. More preferably, an effective amount (suitable dose) will range from 0.1 to 50 mg/kg/day. Treatment may occur before bacterial infection (i.e. prophylaxis), at the start of infection, or after the onset of established symptoms or infection. Treatment with the effective amount may be given 1 to 4 times daily and the typical duration will range from 3 to 10 days, or until bacteria or trypanosoma are no longer present and/or symptoms have disappeared. Furthermore, a suitable topical dose will generally range from approximately 1 nM to 1 mM. Treatment may occur before bacterial infection (.e. prophylaxis), at the start of infection, or after the onset of established symptoms or infection. Treatment with the effective amount may be given 1 to 4 times daily and the typical duration will range from 3 to 10 days, or until bacteria or trypanosoma are no longer present and/or symptoms have disappeared. Those skilled in the art will recognize that deviations from the above described treatment methods and effective amounts are possible and are to be included in the subject matter taught herein.

Furthermore, it is possible that, during therapy, the compounds may be administered alone as pure chemical or as a pure pharmaceutically acceptable salt, analog or derivative. However, it is preferable to provide the active chemical, or its pharmaceutically acceptable salt, analog or derivative, as a pharmaceutical formulation, either as a dry powder (tablet or capsule form or with a suitable carrier), or as a solution or suspension (in water or in physiologically acceptable solvents or cosolvents such as ethanol, propylene glycol, or PEG 400). The appropriate pharmaceutical formulation may be administered by topical, oral, intranasal, intravenous, intramuscular or other appropriate modes. A preferred mode of administration for treating a bacterial infection is to topically apply the inhibitor to the infected region of the subject. The desired dosage (effective amount) may be administered in one or in divided doses at appropriate intervals each day. The compounds and compositions of the invention may also be administered in combination with other therapeutic agents. Those skilled in the art will appreciate that dosages and modes of administration are readily determinable without undue experimentation.

The compounds of the invention may be conveniently formulated into pharmaceutical compositions composed of one or more of the compounds in association with a pharmaceutically acceptable carrier. See, e.g., *Remington's Pharmaceutical Sciences*, latest edition, by E. W. Martin Mack Pub. Co., Easton, Pa., which discloses typical carriers and conventional methods of preparing pharmaceutical compositions that may be used in conjunction with the preparation of formulations of the inventive compounds and which is incorporated by reference herein.

In preferred embodiments, the compounds of the present invention can be delivered in the following manners:

1. Oral/Pill
2. Nasal Aerosol
3. Ear/Eye Drops
4. Topical Cream
5. Intravenous Solution
6. Suppository
7. Dental Mouthwash These methods of drug delivery may be practiced with standard pharmacological formulations.

O. Conditions Treated or Prevented

The compounds of the invention provide a broad range of anti-bacterial and anti-trypanosomal activity. The compounds can inhibit bacterial sialidase and trypanosomal trans-sialidase. The medical benefits which result from inhibition of sialidase/trans-sialidase activity may vary as they are dependent on the specific organism. Examples where sialidase/trans-sialidase activity has been documented to play a role in the pathology are listed below. One skilled in the art would recognize that treatment with the compounds to inhibit the sialidase/trans-sialidase activity in these cases would prove beneficial.

The present compounds can be used in methods of preventing bacterial or trypanosome adherence. In the following examples, the organism requires the sialidase/trans-sialidase activity to attach to the cells of the host prior to invasion. The treatment with compounds would therefore be expected to prevent or limit infection of the host by the microorganism, but not directly kill the microorganism. Treatments, or prophylaxis, of the following infections can be effective:

a) dental caries/bacterial-mediated gum disease [Childs, W. d. & Gibbons, R. J. (1990). Selective modulation of bacterial attachment to oral epithelial cells by enzyme activities associated with poor oral hygiene. *J Period Res.*, 25, pp. 172–8.; Liljemark, W. F., Bloomquist, C. G., Fenner, L. J., Antonelli, P. J. & Coulter, M. C. (1989). Effect of neuraminidase on the adherence to salivary pefficle of *Streptococcus sanguis* and *Streptococcus mitis*. *Caries Res.*, 23, pp. 141–5; Rogers, R., Newbrun, E. & Tatevossian, A. (1979). Neuraminidase activity in human dental plaque fluid. *Archives of Oral Biology* 24(9), 703–5]. Mode of delivery: dental mouthwash;

b) arteritis [Nakato, H., Shinomiya, K. & Mikawa, H. (1986). Possible role of neuraminidase in the pathogenesis of arteritis and thromboctopenia induced in rats by *Erysipelothrix rhusiopathiae*. *Pathol Res Pract.*, 181, pp. 311–9]. Modes of delivery: oral pill, intravenous solution;

c) *Pseudomonas aeruginosa* infection in cystic fibrosis (CF) [Cacalano, G., Kays, M., Saiman, L. & Prince, A. (1992). Production of the *Pseudomonas aeruginosa* neuraminidase is increased under hyperosmolar conditions and is regulated by genes involved in alginate expression. *Journal of Clinical Investigation* 89(6), 1866–74]. Modes of delivery: oral pill, intravenous solution, nasal aerosol;

d) *Actinomyces viscosus* and *A. naeslundii* infection [Costello, A H, Cisar, J, Kolenbrander, P E & Gabriel, O (1979). Neuraminidase-dependent hemagglutination of human erythrocytes by human strains of *Actinomyces viscosus* and *Actinomyces naeslundii*. *Infection & Immunity* 26(2), 563–72]. Modes of delivery: oral pill, intravenous solution, topical cream;

e) *Bacteroides fragilis* infection [Guzman, C. A., Plate, M. & Pruzzo, C. (1990). Role of neuraminidase-dependent adherence in *Bacteroides fragilis* attachment to human epithelial cells. *Fems Microbio Lett.*, 59, pp. 187–92; Namavar, F., Van der Bijl, M. W., Appelmelk, B. J., De Graaff, J. & MacLaren, D. M. (1994). The role of neuraminidase in haemagglutination and adherence to colon WiDr cells by Bacteroides fragilis. *J Med Microbiol.*, 40, pp. 393–6]. Modes of delivery: oral pill, intravenous solution, topical cream; and f) Chagas' Disease, *Trypanosoma cruzi* infection [de Titto & Araujo, 1987; Ming et al., 1993; Prioli et al., 1991]. Modes of delivery: oral pill, intravenous solution.

Furthermore, the inhibitors can be used in the prevention of bacterial vaginosis. In this example, sialidase is highly correlated with the progress of the disease. The most probable role of sialidase is for successful attachment and colonization of the upper and lower genital tract. Therefore, treatment with the compounds would be expected primarily to prevent or slow the progress of bacterial infection to allow the host's immune system time to recover. A second, but important result of treatment with the compounds of the invention would be to reduce the symptoms associated with bacterial vaginosis (rash, itching, discharge, etc.) [Briselden, A. M., Moncla, B. J., Stevens, C. E. & Hillier, S. L. (1992). Sialidases (neuraminidases) in bacterial vaginosis and bacterial vaginosis-associated microflora. *J Clin Microbiol.*, 30, pp. 663–6; McGregor, J. A., et al. (1994). Bacterial vaginosis is associated with prematurity and vaginal fluid mucinase and sialidase: results of a controlled trial of topical clindamycin cream. *Am J Obstet Gynecol.*, 170, pp. 1048–59]. Modes of delivery: topical cream, suppository, oral pill.

Also, the present inhibitors can be used for the prevention of inner ear effusion. Sialidase activity has been correlated with the development of acute and chronic otitis in inner ear effusions. Treatment with the compounds would therefore prevent the damage to the inner ear mucosa and prevent otitis from developing. It would not directly kill the organism causing the infection [LaMarco, K. L., Diven, W. F. & Glew, R. H. (1986). Experimental alteration of chinchilla middle ear mucosae by bacterial neuraminidase. *Ann Otol Rhinol Laryngol.*, 95, pp. 304–8; LaMarco, K. L., Diven, W. F., Glew, R. H., Doyle, W. J. & Cantekin, E. I. (1984). Neuraminidase activity in middle ear effulsions. *Annals of Otology, Rhinology & Laryngology* 93(1 Pt 1), 76–84]. Modes of delivery: Ear drops, oral pill Prevention of arthritis symptoms. Sialidase activity has been correlated with the disease severity in arthritic rats. The effect of treatment with the compounds may reduce the symptoms associated with arthritis, such as lymphocyte activation and swelling [Marchand, N. W., Kishore, G. S. & Carubelli, R. (1978). Neuraminidase activity in the blood and liver of arthritic rats. *Experimental & Molecular Pathology* 19(3), 273–80]. Modes of delivery: oral pill, intravenous solution, topical cream.

Prevention of hemolytic uremic syndrome (HUS) in patients with pneumonia and hemolytic anemia. Sialidases have been implicated as the agent which exposes the *Thomsen cryptantigen*. Treatment with the compounds would reduce the prevalence of patients developing hemolytic uremic syndrome, but not cure the underlying causes [Seger, R., Joller, P., Baerlocher, K., Kenny, A., Dulake, C., Leumann, E., Spierig, M. & Hitzig, W. H. (1980). Hemolytic-uremic syndrome associated with neuraminidase-producing microorganisms: treatment by exchange transfusion. *Helvetica Paediatrica Acta* 35(4), 359–67]. Modes of delivery: oral pill, intravenous solution Prevention of group B streptococci infection in neonates. The high levels of sialidase activity have been associated with severe group B streptococci infection in infants, where streptococci infection can lead to diarrhea, weight loss, or more severe complications. Treatment with the compounds would prevent bacterial spread and reduce the symptoms associated with the disease in infants [Miffigan, T. W., Baker, C. J., Straus, D. C. & Mattingly, S. J. (1978). Association of elevated levels of extracellular neuraminidase with clinical isolates of type imi group B streptococci. *Infection & Immunity* 21(3), 738–46]. Modes of delivery: intravenous solution, suppository Prevention of acute poststreptococcal glomerulonephritis. The sialidase activity of virulent streptococcal infections has been shown to play a role in the development of acute poststreptococcal glomerulonephritis. It would therefore follow that compound treatment would decrease the likelihood of developing acute poststreptococcal glomerulonephritis [Mosquera, J. & Rodriguez-Iturbe, B. (1984). Extracellular neuraminidase production of streptococci associated with acute nephritis. *Clin Nephrol.*, 21, pp. 21–8; Mosquera, J. A., Katiyar, V. N., Coello, J. & Rodriguez-Iturbe, B. (1985). Neuraminidase production by streptococci from patients with glomerulonephritis. *Journal of Infectious Diseases* 151(2), 259–63; Potter, E. V., Shaughnessy, M. A., Poon-King, T. & Earle, D. P. (1982). Streptococcal neuraminidase and acute glomerulonephritis. *Infection & Immunity* 38(3), 1196–1202]. Modes of delivery: intravenous solution, oral pill Prevention of acne and seborrheic eczema. Sialidase activity has been highly associated with Propionibacterium acnes-strains isolated from patients with acne vulgaris, seborrheic eczema and healthy subjects. Treatment with the compounds of the invention should therefore prevent or decrease infection by the Propioniobacterium acnes bacterium. It should also alleviate some of the symptoms associated with acne [Hoffier, U., Gloor, M. & von Nicolai, H. (1981). Neuraminidase production by Propionibacterium acnes-strains isolated from patients with acne vulgaris, seborrheic eczema and healthy subjects. *Zentralblatt Fur Bakteriologie, Mikrobiologie Und Hygiene* 250(1–2), 122–6; von Nicolai, H., Hoffler, U. & Zilliken, F. (1980). Isolation, purification, and properties of neuraninidase from Propionibacterium acnes. *Zentralblait Fur Bakteriologie* 247(1), 84–94]. Modes of delivery: topical cream, oral pill Prevention of arteritis. *Erysipelothrix rhusiopathiae* induced arteritis was highly correlated to production of sialidase by the bacteria. Treatment would therefore inhibit bacterial sialidase, attachment, and infection of aortic tissue. [Nakato et al, 1986; Nakato, H., Shinomiya, K. & Mikawa, H. (1987). Adhesion of Erysipelothrix rhusiopathiae to cultured rat aortic endothelial cells. Role of bacterial neuraminidase in the induction of arteritis. *Pathology, Research & Practice* 182(2), 255–60]. Modes of delivery: oral pill, intravenous solution This invention thus describes classes of bacterial sialidase inhibitors, their pharmaceutically acceptable salts and derivatives, and mixtures thereof having general structure I. These inhibitors may be used in a variety of methods as described herein.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of inhibiting bacterial sialidase comprising administering to a subject an inhibiting effective amount of a compound of formula I:

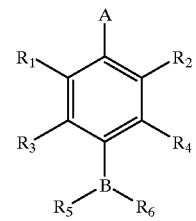

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof.

2. The method of claim 1, wherein A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof.

3. The method of claim 2, wherein one of $R_3$ and $R_4$ is OH the other is $NO_2$.

4. The method of claim 2, wherein one of $R_3$ and $R_4$ is H the other is guanidino.

5. A method of treating a bacterial or trypanosomal infection, comprising administering to a subject a preventative effective amount a compound of formula I:

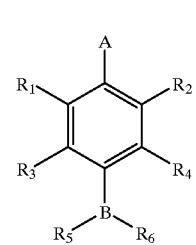

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H, and $R_6$ is $COCH_3$, or $COCl_3$; or an analog, pharmaceutically acceptable salt, derivative, or mixture thereof.

6. The method of claim 5, wherein A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof.

7. A method of preventing a bacterial or trypanosomal infection, comprising administering to a subject a preventative effective amount a compound of formula I:

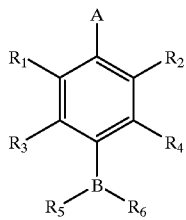

(I)

wherein A is $CO_2H$, $PO_2H$, or $SO_2H$; B is N; $R_1$ and $R_2$ are H; $R_3$ and $R_4$ are, independently, H, OH, $NO_2$, guanidino, or alkyl or alkenyl of from 1 to 3 carbons where the alkyl or alkenyl is unsubstituted or is substituted, independently, with one or more of OH, NH2, or halide; $R_5$ is H; and $R_6$ is $COCH_3$, or $COCl_3$; or an analog, pharmaceutically acceptable salt, derivative, or mixture thereof.

8. The method of claim 7, wherein A is $CO_2H$; $R_3$ and $R_4$ are, independently, H, OH, $NO_2$, or guanidino; $R_5$ is H; and $R_6$ is $COCH_3$, or an analog, pharmaceutically acceptable salt, derivative, or mixture thereof.

9. The method of claim 1, wherein the administering step comprises topical administration.

10. The method of claim 5, wherein the administering step comprises topical administration.

11. The method of claim 7, wherein the administering step comprises topical administration.

* * * * *